US008535944B2

(12) United States Patent
Bamdad

(10) Patent No.: US 8,535,944 B2
(45) Date of Patent: Sep. 17, 2013

(54) **CULTURING EMBRYONIC STEM CELLS, EMBRYONIC STEM-LIKE CELLS, OR INDUCED PLURIPOTENT STEM CELLS WITH A MUC1 OR MUC1* LIGAND**

(75) Inventor: Cynthia C. Bamdad, Boston, MA (US)

(73) Assignee: Minerva Biotechnologies Corporation, Waltham, MA (US)

( * ) Notice: Subject to any disclaimer, the term of this patent is extended or adjusted under 35 U.S.C. 154(b) by 0 days.

(21) Appl. No.: 12/814,420

(22) Filed: Jun. 11, 2010

(65) Prior Publication Data

US 2010/0316688 A1 Dec. 16, 2010

Related U.S. Application Data

(60) Provisional application No. 61/186,310, filed on Jun. 11, 2009, provisional application No. 61/323,779, filed on Apr. 13, 2010.

(51) Int. Cl.
*C12N 5/00* (2006.01)

(52) U.S. Cl.
USPC .......................................... 435/384; 435/395

(58) Field of Classification Search
None
See application file for complete search history.

(56) References Cited

U.S. PATENT DOCUMENTS

| | | | |
|---|---|---|---|
| 5,834,217 | A | 11/1998 | Levine |
| 7,129,058 | B2 | 10/2006 | Yamashita |
| 2002/0119568 | A1 | 8/2002 | Berenson et al. |
| 2003/0036199 | A1 | 2/2003 | Bamdad |
| 2004/0067585 | A1 | 4/2004 | Wang et al. |
| 2006/0252087 | A1 | 11/2006 | Tang et al. |
| 2007/0134713 | A1 | 6/2007 | Cao |
| 2009/0075926 | A1 | 3/2009 | Bamdad |
| 2009/0142790 | A1 | 6/2009 | Fang et al. |

FOREIGN PATENT DOCUMENTS

| | | | |
|---|---|---|---|
| WO | 96/00782 | A1 | 1/1996 |
| WO | 02/056022 | A2 | 7/2002 |
| WO | 03/074074 | A1 | 9/2003 |
| WO | 2004/022590 | A2 | 3/2004 |
| WO | 2005/019269 | A2 | 3/2005 |
| WO | 2006/105448 | A2 | 10/2006 |
| WO | 2007/053135 | A1 | 5/2007 |

OTHER PUBLICATIONS

Jiang X S et al., "Surface-immobilization of adhesion peptides on substrate for ex vivo expansion of cryopreserved umbilical cord blood CD34+cells," Biomaterials, Elsevier Science Publishers BV., 27(13): 2723-2732, May 1, 2006.
Dellatore S M et al., "Mimicking stem cell niches to increase stem cell expansion," Current Opinion in Biotechnology, 19(5): 534-540, Oct. 1, 2008.
Makino H et al., "Immobilization of leukemia inhibitory factor (LIF) to culture murine embryonic stem cells," Journal of Bioscience and Bioengineering, 98(5): 374-379, Jan. 1, 2004.
Al-Hajj et al., "Prospective Identification of Tumorigenic Breast Cancer Cells," PNAS, 100(7):3983-3988, 2003.
Al-Hajj et al., "Self Renewal and Solid Tumor Stem Cells," Oncogene, 23:7274-7282, 2004.
Barratt-Boyes et al., "Immunization of Chimpanzees with Tumor Antigen MUC1 Mucin Tandem Repeat Peptide Elicits Both Helper and Cytotoxic T-Cell Responses1," Clinical Cancer Research, 5:1918-1924, 1999.
Bonnet et al., "Human Acute Myeloid Leukemia is Organized as a Hierarchy that Originates from a Primitive Hematopoietic Cell," Nature Medicine, 3(7):730-737, 1997.
Briasoulis et al., "G-CSF Induces Elevation of Circulating CA 15-3 in Breast Carcinoma Patients Treated in an Adjuvant Setting," American Cancer Society, 91(5):909-917, 2001.
Burchell et al., "Development and Characterization of Breast Cancer Reactive Monoclonal Antibodies Directed to the Core Protein of the Human Milk Mucin," Cancer Res., 47:5476-5482, 1987.
Byrd et al., "Mucins and Mucin Binding Proteins in Colorectal Cancer," Cancer and Metastasis Reviews, 23:77-99, 2004.
Clarke, R. B., "Isolation and Characterization of Human Mammary Stem Cells," Cell Prolif., 38:375-386, 2005.
Cloosen et al., "Mucin-1 is Expressed on Dendritic Cells, both In Vitro and In Vivo," International Immunology, 16(11):1561-1571, 2004.
Gad et al., MUC1-Derived Glycopeptide Libraries with Improved MHC Anchors are Strong Antigens and Prime Mouse T Cells for Proliferative Responses to Lysates of Human Breast Cancer Tissue, Eur. J. Immunol., 33: 1624-1632, 2003.
Gendler et al., "Molecular Cloning and Expression of Human Tumor-Associated Polymorphic Epithelial Mucin," The Journal of Biological Chemistry, 265(25):15286-15293, 1990.
Gervasi et al., "nm23 Influences Proliferation and Differentiation of PC12 Cells in Response to Nerve Growth Factor1," Cell Growth and Differentiation, 7:1689-1695, 1996.
Hanisch, F.-G., "Design of a MUC1-Based Cancer Vaccine," Biochemical Society, 33(4):705-708, 2005.
Hikita et al., "MUC1* Mediates the Growth of Human Pluripotent Stem Cells," PLoS One, 3(10):1-13, 2008.
Jarrard et al., "MUC1 is a Novel Marker for the Type II Pneumocyte Lineage during Lung Carcinogenesis," Cancer Res., 58:5582-5589, 1998.
Kim et al., "Point Mutations Affecting the Oligomeric Structure of Nm23-H1 Abrogates its Inhibitory Activity on Colonization and Invasion of Prostate Cancer Cells," Biochemical and Biophysical Research Communications, 307:281-289, 2003.
Kufe et al., "Differential Reactivity of a Novel Monoclonal Antibody (DF3) with Human Malignant Versus Benign Breast Tumors," Hybridoma, 3(3):223-232, 1984.
Lakso, M., "Embryonic Expression of nm23 during Mouse Organonesis," Cell Growth & Differentiation, vol. 3: 873-879, Dec. 1992.
Lapidot et al., "A Cell Initiating Human Acute Myeloid Leukaemia after Transplantation into SCID Mice", Letters to Nature, 367:645-648, 1994.

(Continued)

*Primary Examiner* — Deborah Crouch
(74) *Attorney, Agent, or Firm* — Joseph Hyosuk Kim; JHK Law

(57) ABSTRACT

The present application describes a method of culturing, expanding or growing stem or stem-like cells or induced pluripotent stem cells on a surface, including attaching the cells to the surface through a ligand that binds to the surface and the cells.

36 Claims, 20 Drawing Sheets

(56) References Cited

OTHER PUBLICATIONS

Lascu et al., "Quaternary Structure of Nucleside Diphosphate Kinases," Journal of Bioenergetics and Biomembranes, 32(3): 227-236, 2000.
Leong et al., "Epithelial Membrane Antigen (EMA) or MUC1 Expression in Monocytes and Monoblasts," Pathology, 35(5):422-427, 2003.
Ligtenberg et al., "Episialin, a Carcinoma-associated Mucin, is Generated by a Polymorphic Gene Encoding Splice Variants with Alternative Amino Termini*", The Journal of Biological Chemistry, 265(10):5573-5578, 1990.
Lombardi et al., "nm23: Unraveling its Biological Function in Cell Differentiation," Journal of Cellular Physiology, 182:144-149, 2000.
Luong et al., "Expression of Nm23-H1 in AML correlates with White Cell Count at Diagnosis and in Vitro Acts as a Survival Factor for Primary AMLs cells; Evidence of a Novel Autocrine Survival Factor in AML," XP-001193730, 102 (11):611a, 2003.
MacDonald et al., "Site-Directed Mutagenesis of nm23-H1," The Journal of Biological Chemistry, 271(41):25107-25116, 1996.
Mahanta et al., "A Minimal Fragment of MUC1 Mediates Growth of Cancer Cells," PLoS One, 3(4):1-12, 2008.
Matsui et al., "Characterization of Clonogenic Multiple Myeloma Cells", Blood, 103(6):2332-2336, 2004.
Meseguer et al., "Human Endometrial Mucin MUC1 is Up-Regulated by Progesterone and Down-Regulated in Vitro by the Human Blastocyst," Biology of Reproduction, 64:590-601, 2001.
Miyaki et al., "Overexpression of nm23-H2/NDP Kinase B in a Human Oral Squamous Cell Carcinoma Cell Line Results in Reduced Metastasis, Differentiated Phenotype in the Metastatic Site, and Growth Factor—Independent Proliferative Acticity in Culture," Clin. Cancer Res., 5:4301-4307, 1999.
Negroni et al., "Neuroblastoma Specific Effects of DR-nm23 and its Mutant Forms on Differentiation and Apoptosis," Cell Death and Differentiation, 7:843-850, 2000.
Okabe-Kado et al., "A New Function of Nm23/NDP Kinase as a Differentiation Inhibitory Factor, Which Does Not Require it's Kinase Activity," FEBS Letters, 363:311-315, 1995.
Okabe-Kado et al., "Characterization of a Differentiation-Inhibitory Activity from Nondifferentiating Mouse Myeloid Leukemia Cells," Cancer Research, 45:4848-4852, 1985.
Okabe-Kado et al., "Identity of a Differentiation Inhibiting Factor for Mouse Myeloid Leukemia Cells with NM23/Nucleoside Diphosphate Kinase," Biochemical and Biophysical Research Communications, 182(3):987-994, 1992.
Okabe-Kado et al., "Inhibitory Action of nm23 Proteins on Induction of Erythroid Differentiation of Human Leukemia Cells," Biochimica et Biophysica Acta., 1267:101-106, 1995.
Okabe-Kado et al., "Physiological and Pathological Relevance of Extracellular NM23/NDP Kinases," Journal of Bioenergetics and Biomembranes, 35(1):89-93, 2003.
Rughetti et al., "Regulated Expression of MUC1 Epithelial Antigen in Erythropoiesis," British Journal of Haematology, 120:344-352, 2003.
Singh et al., "Identification of a Cancer Stem Cell in Human Brain Tumors," Cancer Res., 63:5821-5828, 2003.
Sorscher, S.M., "Microinjection of an NM23 specific antibody inhibits cell division in rat embryo fibroblasts," Biochemical and Biophysical Research Communications, 195(1): 336-345, 1993.
Spicer et al., "Molecular Cloning and Analysis of the Mouse Homologue of the Tumor-associated Mucin, MUC1, Reveals Conservation of Potential O-Glycosylation Sites, Transmembrane, and Cytoplasmic Domains and a Loss of Minisatellite-Like Polymorphism," The Journal of Biological Chemistry, 266(23):15099-15109, 1991.
Stingl et al., "Epithelial Progenitors in the Normal Human Mammary Gland," Journal of Mammary Gland Biology and Neoplasia, 10(1):49-59, 2005.
Thathiah et al., "Tumor Necrosis Factor-α Converting Enzyme/ADAM 17 Mediates MUC1 Shedding," J. Biol. Chem., 278:3386-3394, 2003.
Thathiah et al., "Tumor Necrosis Factor α Stimulates MUC1 Synthesis and Ectodomain Release in a Human Uterine Epithelial Cell Line," Endocrinology, 145(9):4192-4203, 2004.
Vacanti et al., "Identification and Initial Characterization of Spore-Like Cells in Adult Mammals," Journal of Cellular Biochemistry, 80:455-460, 2001.
Venturelli et al., "Overexpression of DR-nm23, a Protein Encoded by a Member of the nm23 Gene Family, Inhibits Granulocyte Differentiation and Induces Apoptosis in 32Dc13 Myeloid Cells," Pro. Natl. Acad. Sci. USA, 92:7435-7439, 1995.
Willems et al., Extracellular Nucleoside Diphosphate Kinase NM23/NDPK Modulates Normal Hematopoietic Differentiation, Experimental Hematology, 30:640-648, 2002.
Willems et al., "Decrease in Nucleoside Diphosphate Kinase (NDPK/nm23) Expression During Hematopoietic Maturation*," The Journal of Biological Chemistry, 273(22):13663-13668, 1998.
Wright et al., "Cytotoxic T Lymphocytes from Humans with Adenocarcinomas Stimulated by Native MUC1 Mucin and a Mucin Peptide Mutated at a Glycosylation Site," Journal of Immunotherapy, 23(1):2-10, 2000.
Zhong et al., "Evaluation of MUC1 and EGP40 in Bone Marrow and Peripheral Blood as a Marker for Occult Breast Cancer," Arch Gynecol Obstet, 264:177-181, 2001.
Zotter et al., "Monoclonal Antibodies to Epithelial Sialomucins Recognize Epitopes at Different Cellular Sites in Adenolymphomas of the Paratid Gland," Int. J. Cancer Suppl., 3:38-44, 1988.

A B C D

Figure 11 hu ES H9s Growing Attached to Histidine-Tagged Ligands that Bind to Stem Cell Surface Proteins - Images Captured Day 3 Post Plating

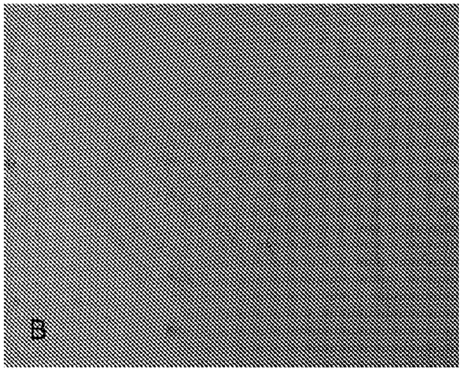

NM23 ON SURFACE
8nM NM23 + Ca CM
19 undifferentiated/ 1 differentiated

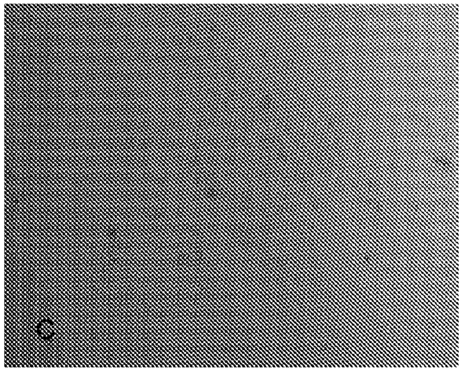

RGD PEPTIDE ON SURFACE
8nM NM23 + Ca CM
13 undifferentiated/ 2 differentiated

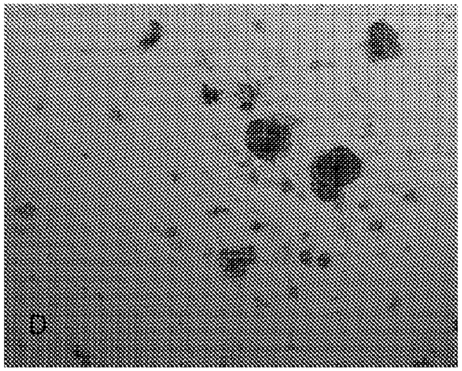

RGD PEPTIDE ON SURFACE
4ng/ml bFGF + HS27 CM
3 undifferentiated/ 1 differentiated

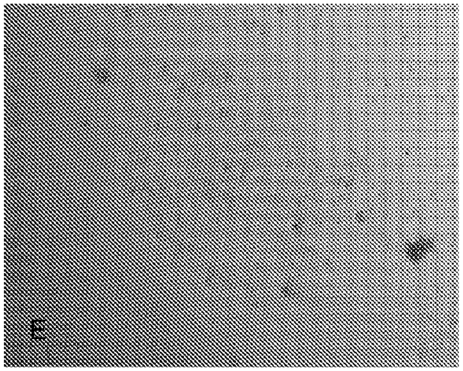

PROTEIN G,
ANTI-SSEA4 ON SURFACE
8nM NM23 + Ca CM
13 undifferentiated/ 2 differentiated

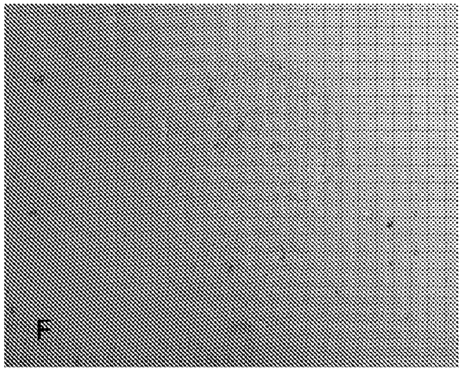

PROTEIN G,
ANTI-Tra 1-81 ON SURFACE
8nM NM23 + Ca CM
19 undifferentiated/ 1 differentiated

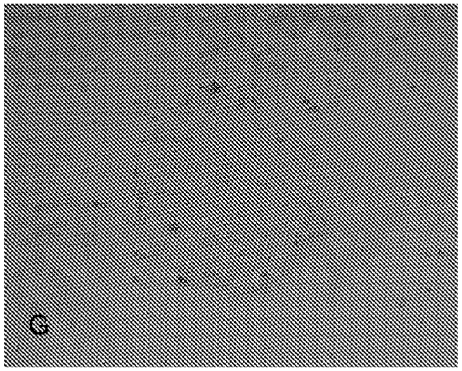

RGD PEPTIDE ON SURFACE
4ng/ml bFGF + Ca CM
14 undifferentiated/ 1 differentiated

SEQUENCE LISTING

```
<160> NUMBER OF SEQ ID NOS: 5

<210> SEQ ID NO 1
<211> LENGTH: 45
<212> TYPE: PRT
<213> ORGANISM: Artificial Sequence
<220> FEATURE:
<223> OTHER INFORMATION: Primary Sequence of the MUC1 Growth Factor
      Receptor

<400> SEQUENCE: 1

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala
        35                  40                  45
```

-continued

<210> SEQ ID NO 2
<211> LENGTH: 45
<212> TYPE: PRT
<213> ORGANISM: Artificial Sequence
<220> FEATURE:
<223> OTHER INFORMATION: variant of the PSMGFR peptide

<400> SEQUENCE: 2

```
Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser Asp Val Pro Phe Pro Phe Ser Ala Gln Ser Gly Ala
        35                  40                  45
```

<210> SEQ ID NO 3
<211> LENGTH: 35
<212> TYPE: PRT
<213> ORGANISM: Artificial Sequence
<220> FEATURE:
<223> OTHER INFORMATION: N-10 PSMGFR

<400> SEQUENCE: 3

```
Gln Phe Asn Gln Tyr Lys Thr Glu Ala Ala Ser Arg Tyr Asn Leu Thr
1               5                   10                  15

Ile Ser Asp Val Ser Val Ser Asp Val Pro Phe Pro Phe Ser Ala Gln
            20                  25                  30

Ser Gly Ala
        35
```

<210> SEQ ID NO 4
<211> LENGTH: 35
<212> TYPE: PRT
<213> ORGANISM: Artificial Sequence
<220> FEATURE:
<223> OTHER INFORMATION: C-10 PSMGFR

<400> SEQUENCE: 4

```
Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val
        35
```

<210> SEQ ID NO 5
<211> LENGTH: 31
<212> TYPE: PRT
<213> ORGANISM: Artificial Sequence
<220> FEATURE:
<223> OTHER INFORMATION: RGD peptide

<400> SEQUENCE: 5

```
His His His His His His Ser Ser Ser Ser Gly Ser Ser Ser Ser Gly
1               5                   10                  15

Ser Ser Ser Ser Gly Gly Arg Gly Asp Ser Gly Arg Gly Asp Ser
            20                  25                  30
```

CULTURING EMBRYONIC STEM CELLS, EMBRYONIC STEM-LIKE CELLS, OR INDUCED PLURIPOTENT STEM CELLS WITH A MUC1 OR MUC1* LIGAND

CROSS-REFERENCE TO RELATED APPLICATIONS

The present application claims the benefit of priority to U.S. Provisional Patent Application No. 61/186,310, filed Jun. 11, 2009, and 61/323,779, filed Apr. 13, 2010, the contents of which are incorporated by reference in their entirety.

BACKGROUND OF THE INVENTION

A problem that exists in the field of culturing or proliferating stem cells, progenitors, induced pluripotent stem cells or other non-adherent cells, is how to culture the cells in a way that will not interfere with later intended uses, including transplants or downstream differentiation. Unlike most cells that adhere to plastic, which can be cultured in plastic growth flasks, stem cells are non-adherent, therefore cannot be grown using traditional methods. Stem cells will, however, grow on layers of fibroblast cells. These "feeder cell" layers provide a surface for adhesion and feed the cells with a mixture of as yet uncharacterized growth factors that are required for stem cell growth and survival. More recently, researchers have been able to culture stem cells by attaching them to components derived from the extracellular matrix, such as matrigel. Stem cells adhere to these surface-like substrates but must be cultured in growth media that contains both basic fibroblast growth factor (bFGF) and collected secretions from fibroblast feeder cells. It is not entirely clear how or why these methods promote stem cell proliferation, since they both use a milieu of uncharacterized factors secreted by cells. It has been reported that stem cells differentiate more quickly when they are cultured over matrigel surfaces. Stem cells grown according to either method, i.e. feeder cells or matrigel plus conditioned media from feeder cells, spontaneously differentiate. Differentiating stem cells secrete factors that induce neighboring cells to also initiate differentiation. Therefore, every approximately 7 days, a technician must manually dissect and harvest only those stem cell colonies or colony portions that appear to be undifferentiated. The harvested cells are then re-plated for continued growth. This procedure is repeated until enough undifferentiated cells can be harvested for the intended purpose. These methods for culturing stem cells are the state of the art for the industry.

Virtually any kind of scaled up growth of stem cells or induced pluripotent stem cells will require the development of new methods that enable high throughput harvesting of these cells.

The current practice is to grow stem cells on fibroblast feeder cells from which the only method of harvesting is by manual dissection, under a microscope, and isolation of "good" cells, followed by re-plating. This procedure is flawed because it is subjective and time consuming. What is needed are methods for automatable harvesting and automatable methods for purifying the desired cells from a mixed pool wherein cells are selected on the basis of molecular recognition rather than subjective criteria of a technician.

The state of the art methods for culturing stem cells are inadequate because they: 1) are labor-intensive; 2) are inherently incompatible with large scale growth; 3) depend on uncharacterized factors such as conditioned media; 4) require cells or cellular products for adhering stem cells to growth flasks; and 5) frequently use non-human cells and cellular extracts that can irreversibly change the human stem cells. A significant improvement would be if discrete factors that enable stem cell growth were identified. It is thought that if only the necessary and sufficient growth factors were added, then spontaneous differentiation would be minimized. Another significant improvement would be if cells could be safely harvested in a manner that was compatible with large scale growth rather than the current method of manual dissection under a microscope. Currently, stem cells growing on matrigel can be harvested by enzymatic cleavage, e.g. using trypsin. Typically, undifferentiated colonies or portions of colonies are manually dissected then digested with an enzyme such as trypsin or collagenase. However, trypsin causes significant cell death and serial passaging of stem cells on matrigel has been reported to cause abnormal karyotype. This could be due to harvesting with trypsin or may be due to the fact that matrigel is a mixture of cells and secretions from mouse sarcoma cells. Non-human feeder cells have been suspected of altering the resultant stem cells so that they are not entirely human. For example, it is suspected that glycosylation patterns and other post-translational modifications may take on characteristics of the feeder cell species.

Thus it would be a great improvement over the state of the art if cell-free methods were developed that support stem cell growth. An even greater improvement would be if stem cells could be grown and harvested using fully characterized, discrete agents wherein as many as possible are synthetic agents. For producing cells suitable for human therapies, it would be a great improvement over the state of the art if methods were developed for culturing the cells that is comprised solely of definable factors. Ideally, the defined components should be free of non-human components. Recombinant proteins, or synthetic components are preferred. Antibodies, including polyclonal, monoclonal, humanized, chimeras or derivatives thereof are especially preferred because their production is highly reproducible, they are robust and they can be readily removed from the harvested cells, for example by affinity depletion using Protein A or Protein G.

SUMMARY OF THE INVENTION

The present invention is directed to a method of culturing, expanding or growing stem or stem-like cells or induced pluripotent stem cells on a surface, comprising attaching the cells to the surface through a ligand that binds to the surface and the cells. The ligand may bind to the surface directly or indirectly through an intermediary. The intermediary may be a chemical linker or another protein or a combination thereof. The protein may be protein A or protein G. In particular, the linker may be photo or chemically sensitive. And the ligand or the intermediary may be non-specifically adsorbed to the surface, or may be covalently coupled or attached to the surface through an affinity tag-binding partner interaction. The ligand may also be linked to a polymer. In a particular embodiment, the ligand may specifically bind to a polypeptide that is expressed on the stem or stem-like cells or induced pluripotent stem cells. The polypeptide on the surface of the cell may be MUC1 or MUC1*, SSEA3, SSEA4, Tra 1-81 or Tra 1-60. The ligand may be an antibody or a growth factor. Preferably, the antibody may specifically bind to PSMGFR or C-10 PSMGFR. Preferably, the growth factor may be wild-type NM23, or NM23-S120G mutant, or bFGF.

In another aspect, the present invention is directed to a method for culturing stem or stem-like cells or induced pluripotent stem cells, wherein the cells are exposed to a medium containing agents that bind to a peptide having the sequence of PSMGFR. In this respect, the agent may be an antibody, or the agent may be wild-type NM23 or NM23-S120G mutant.

In yet another embodiment, the present invention is directed to a method of culturing stem or stem-like cells or induced pluripotent stem cells comprising exposing the cells to medium containing agents secreted from MUC1*-positive cancer cells. The MUC1*-positive cells may be T47D, ZR-75-30, or ZR-75-1.

In yet another aspect, the invention is directed to a method of culturing stem or stem-like cells or induced pluripotent stem cells comprising exposing the cells to conditioned media from MUC1*-positive cancer cells. The MUC1*-positive cells may be in particular T47D, ZR-75-30, or ZR-75-1.

In one aspect, the surface that is to be used may be preferably not matrigel, and with the presence of fibroblast feeder cells, nor manual dissection process when the cells are removed.

In another aspect, the present invention is directed to a method of harvesting cells from cells grown according to the method above, comprising adding a competing molecule that binds to the ligand so that the cells are released from binding to the ligand or the surface.

In yet another aspect, the present invention is directed to a method of harvesting cells from cells grown according to the method indicated above, comprising cleaving a linker bound to the surface that is directly or indirectly attached to the cells, so that the cells are released from the surface.

In yet another aspect, the present invention is directed to a method of identifying state of differentiation of cells comprising using anti-MUC1* antibody to bind to the cells, wherein positive signal for anti-MUC1* antibody indicates pluripotent cell state, and cells showing binding to non-clipped MUC1 indicates differentiated cell state. This method may further include separating cells from a mixed population of stem and stem-like cells or induced pluripotent stem cells and newly differentiating cells, comprising using anti-MUC1* antibody to bind to the cells, wherein positive signal for anti-MUC1* antibody indicates a pluripotent cell state, and cells showing binding to non-clipped MUC1 indicates differentiated cell state. In particular, this method may further include contacting the cells with antibodies to stem or stem-like cell or induced pluripotent stem cell markers, wherein positive signal for a stem or stem-like cell or induced pluripotent stem cell marker indicates the presence of pluripotent stem cell state. In particular, the cells may be contacted with anti-MUC1* and anti-Tra 1-81, anti-Tra 1-60, SSEA3 or SSEA4 antibodies.

In yet another aspect, the present invention is directed to a method of detecting cancer stem cells using anti-MUC1* antibody to bind to the cells, wherein positive signal for anti-MUC1* antibody indicates cancer stem cells. This method may further include contacting the cells with antibodies to stem cell markers, wherein positive signal for a stem cell marker indicates the presence of cancer stem cells.

In yet another aspect, the present invention is directed to a method of modulating culturing, expanding or growing and inhibiting differentiation of stem or stem-like cells or induced pluripotent stem cells on a surface, comprising attaching the cells to the surface directly or indirectly through a ligand that binds to the cells, and exposing the cells to a medium containing agents that bind to a peptide having the sequence of PSMGFR. The agent may dimerize MUC1* to promote growth and inhibit differentiation, or the agent may inhibit dimerization of MUC1* to promote differentiation.

In yet another aspect, the present invention is directed to a method of separating cell types, comprising: creating a spatial address on a surface for a variety of ligands having affinity for a different cell type or for specific markers that identify a cell stage or type; and adding the cells to the surface, wherein the cells are spatially separated depending on which ligand the cells bind. The surface may be a particle or a nanoparticle.

In yet another aspect, the present invention is directed to a method of implanting into a host body, a surface having ligands attached that are ligands of stem or stem-like cells or induced pluripotent stem cells. The host may be a patient. In particular, the ligands may be growth factors for the host's stem or stem-like cells or induced pluripotent stem cells.

In yet another aspect, the present invention is directed to a method of implanting into a host body, a surface having cells attached through ligands that bind to the surface and the cells.

In yet another aspect, the present invention is directed to a method of proliferating stem or stem-like cells or induced pluripotent stem cells in vivo, comprising administering to a host body a surface having ligands attached that are ligands of stem or stem-like cells or induced pluripotent stem cells.

In yet another aspect, the present invention is directed to a composition comprising: a surface on which is bound protein A or protein G via an affinity interaction, wherein the protein A or protein G is bound to an antibody specific for a polypeptide expressed specifically on a stem or stem-like cell or induced pluripotent stem cell, and a MUC1* dimerizing agent. The affinity interaction may be via NTA-Ni interaction to the surface. The polypeptide may be MUC1 or MUC1*, SSEA3, SSEA4, Tra 1-81 or Tra 1-60. The MUC1* dimerizing agent may be wild-type NM23 or NM23-S120G mutant.

In yet another aspect, the present invention is directed to a method of proliferating stem or stem-like or induced pluripotent stem cell, comprising: contacting a surface on which is bound protein A or protein G via an affinity interaction, wherein the protein A or protein G is bound to an antibody specific for a polypeptide expressed specifically on a stem or stem-like cell or induced pluripotent stem cell, with a sample containing the cells and with a MUC1* dimerizing agent.

BRIEF DESCRIPTION OF THE DRAWINGS

FIGS. 6A1-D2 show photos of hu ES H9s cells growing on anti-MUC1* antibody surfaces: A) cultured in minimal media alone at day 3 (A1) and day 7 (A2); B) minimal media plus 80 ng/ml anti-MUC1* at 3 days (B1) and 7 days (B2); C) in 4 ng/ml bFGF and 50% conditioned media from HS27 fibroblasts at day 3 (C1) and day 7 (C2); D1, D2) cells from well A and B were harvested by adding free PSMGFR (MUC1* extra cellular domain) peptide, which released the cells from the surface; cells were re-plated on fresh anti-MUC1* antibody surfaces where they attached and proliferated.

FIGS. 11A-11G show that stem cells adhere and are cultured on surfaces coated with NTA-Ni, to which first were bound histidine-tagged ligands NM23, an RGD peptide, and Protein G, followed by anti-SSEA4 and Tra 1-81. Hu ES H9 cell growth and colony formation followed. Undifferentiated and differentiated colony numbers counted at day 3 were plotted (B-G). Photos of representative stem cells colonies that were plotted in FIG. 11A.

FIG. 15C. However, when the cells differentiated, the reverse MUC1 pattern was detected. No MUC1* staining or OCT4 staining was observed (FIG. 15D, 15E). But every cell stained positive for the full-length MUC1 (FIG. 15F). Similarly, undifferentiated stem cells stained positive for NM23, the ligand of MUC1* and NM23 exactly co-localized with MUC1*, and OCT4 (FIGS. 15G-15L).

DETAILED DESCRIPTION OF THE INVENTION

Figure 1:
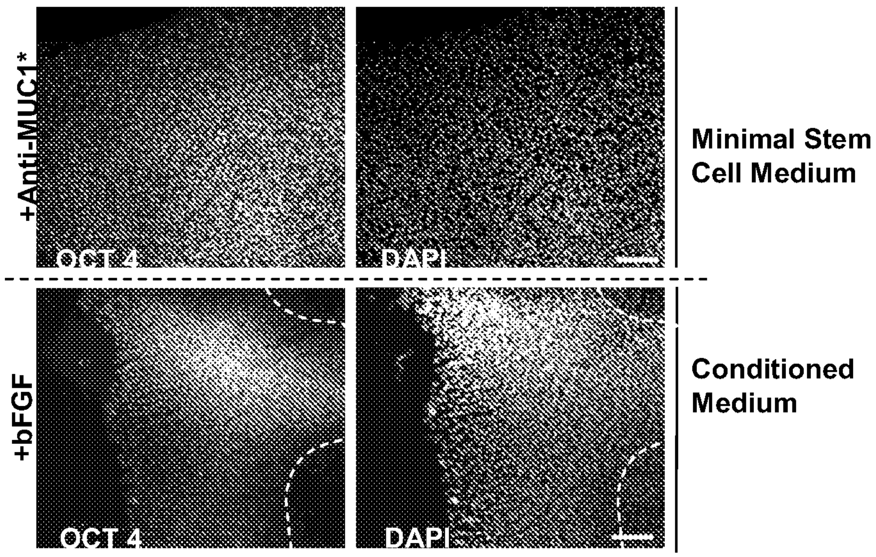
FIG. 1 shows that human embryonic stem cells (H9s) attached to matrigel grow essentially 100% pluripotent (OCT4+) when cultured in anti-MUC1* in minimal media, compared to lesser cell numbers and more differentiation when cultured in the standard bFGF and conditioned media from fibroblast feeder cells. DAPI stains the nuclei of all cells. Dotted lines demark the border of the undifferentiated portion of the colony. In wells treated with anti-MUC1*, undifferentiated stem cells grew to the limits of the wells.

In the present application, "a" and "an" are used to refer to both single and a plurality of objects.

As used herein, "MUC1 Growth Factor Receptor" (MGFR) is a functional definition meaning that portion of the MUC1 receptor that interacts with an activating ligand, such as a growth factor or a modifying enzyme such as a cleavage enzyme. The MGFR region of MUC1 is that extracellular portion that is closest to the cell surface and is defined by most or all of the PSMGFR, as defined below. The MGFR is inclusive of both unmodified peptides and peptides that have undergone enzyme modifications, such as, for example, phosphorylation, glycosylation and so forth.

As used herein, "Primary Sequence of the MUC1 Growth Factor Receptor" (PSMGFR) refers to peptide sequence that defines most or all of the MGFR in some cases, and functional variants and fragments of the peptide sequence. The PSMGFR is defined as SEQ ID NO:1, and all functional variants and fragments thereof having any integer value of amino acid substitutions up to 20 (i.e. 1, 2, 3, 4, 5, 6, 7, 8, 9, 10, 11, 12, 13, 14, 15, 16, 17, 18, 19, or 20) and/or any integer value of amino acid additions or deletions up to 20 at its N-terminus and/or C-terminus. A "functional variant or fragment" in the above context refers to such variant or fragment having the ability to specifically bind to, or otherwise specifically interact with, ligands that specifically bind to, or otherwise specifically interact with, the peptide of SEQ D NO:1, while not binding strongly to identical regions of other peptide molecules identical to themselves, such that the peptide molecules would have the ability to aggregate (i.e. self-aggregate) with other identical peptide molecules. One example of a PSMGFR that is a functional variant of the PSMGFR peptide of SEQ NO:1 is SEQ ID NO:2, which differs from SEQ ID NO:1 by including an -SPY-sequence instead of the -SRY-.

As used herein, "MUC1*" refers to the MUC1 protein with the N-terminus truncated such that the extracellular domain is essentially comprised of the PSMGFR (SEQ ID NO: 1).

As used herein, a "surface" as used in the context of the cell being bound to a surface can be a solid substrate, or porous substrate or other non-solid substrates.

As used herein, "minimal media" can be any media that contain the minimum nutrients possible for cell culture, generally without the presence of a mixture of undefined agents, such as conditioned media from cells, or serum from a live host. As used herein, "minimal stem cell growth media" can be any media that contain the minimum nutrients possible for stem cell or stem-like cell culture, This is also referred to as minimal media or MM. As can be seen minimal media as used in the present invention is not limited to the exemplified minimal media and can encompass numerous types of solutions with defined components.

As used herein, "stem-like" cells have some of the characteristics of stem cells. For example, they have some ability to self-renew. They either: a) express, or are induced to express, OCT4, SOX2, and NANOG, or KLF4; or b) they express high levels of MUC1* on their surface. Examples of stem-like cells include but are not limited to progenitor cells, multipotent stem cells, cells undergoing process to induce pluripotency, cancer cells, cancer stem cells, hematopoietic stem cells, iPS, and some antibody producing hybridoma cells.

As used herein, "induced pluripotent stem cells" or "iPS" refers to a type of pluripotent stem cell artificially derived from a non-pluripotent cell, typically an adult somatic cell, by inducing a "forced" expression of certain genes.

As used herein, "MUC1* stimulator" refers to any molecule that is able to activate the activity of MUC1*, such as dimerization of MUC1* or cleavage of MUC1 to form MUC1*.

Sequence Listing Free Text

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

GTINVHDVETQFNQYKTEAASRYNLTISDVSVSDVPFPFSAQSGA (SEQ ID NO:1) describes the membrane proximal extracellular region of MUC1 from amino acid 1110 to 1155 (PSMGFR). GTINVHDVETQFNQYKTEAASPYNLTISDVSVSDVPFPFSAQSGA (SEQ ID NO:2) describes a variant of the membrane proximal extracellular region of MUC1 from amino acid 1110 to 1155 (variant of PSMGFR). QFNQYKTEAASRYNLTISDVSVSDVPFPFSAQSGA (SEQ ID NO:3) describes the PSMGFR sequence with ten amino acids at the N terminus deleted (N-10 PSMGFR).

GTINVHDVETQFNQYKTEAASRYNLTISDVSVSDV (SEQ ID NO:4) describes the PSMGFR sequence with ten amino acids at the C terminus deleted (C-10 PSMGFR).

Stem or Stem-Like Cell or Induced Pluripotent Stem Cell on a Surface

The present invention discloses methods for culturing or expanding stem, or stem-like cells or induced pluripotent stem cells and progenitors that involve attaching ligands to cell surface proteins onto solid supports that can either hold growth medium or that can be added to growth medium.

The present invention discloses new methods and surfaces for culturing cells. The methods are especially useful for growing and maintaining cells that are not adherent. These methods are particularly useful for culturing stem, stem-like and progenitor cells.

Surfaces

The present invention discloses new surfaces and methods for growing cells. These surfaces are particularly useful for culturing non adherent cells, stem cells and stem-like cells, including induced pluripotent stem (iPS) cells and some progenitor cells. Methods disclosed herein solve the problem of how to retain valuable cells while exchanging cell culture media. Many of the existing cell culture methods work for adherent cells because they attach to the flask surface. Old liquid medium can be removed and replaced with new medium without disturbing the cells that are attached to the surfaces of the containment vessel. Some methods of the invention are also useful in that they allow for the retention of valuable growth factors, while less expensive factors that need to be replaced more frequently are exchanged. Other methods of the invention provide for greater surface area for cell attachment and thereby increase the yield of cells while using a relatively small space and a small volume of culture medium. The methods in general involve attaching, either directly or indirectly, ligands to a surface wherein the ligands are able to bind to molecules on the cell surface.

Surfaces that are suitable for use with these methods can be membranes or porous in nature. Surfaces described herein can be polymers, surfaces coated with polymers, cyclodextrin or cyclodextran. The surfaces may be spatially addressable surfaces, surface of beads, particles, or nanoparticles. The beads, particles or nanoparticles can be free in solution or connected by intervening molecules. For example a membrane, can be comprised of a polymeric substance and may have attached thereto beads or particles bearing ligands that promote binding between cells and the surface. The invention includes the use of these surfaces for in vitro, ex vivo and in vivo growth. Surfaces of the invention can be used to culture cells in vitro. Alternatively, surfaces of the invention can be implanted in a host. The surfaces can bear cells, such as stem cells, that are implanted as a therapy. For example, surfaces of the invention with or without growing stem cells attached can be transplanted so that the surface increases the efficiency of engraftment. In another case, the transplanted surface bears ligands to recruit the host's own cells or stem cells to an area or to promote the growth of targeted cells at that location. For example, surfaces that attract and promote the growth of stem cells can be inserted into a joint to encourage the replacement of cartilage. Surfaces of the invention can be shaped or coated onto a scaffold such that the cells eventually form a 3-dimensional form. For example, a material can be made into the shape of an ear then coated with one of the surfaces described herein that enable to attachment and growth of stem or stem-like cells that eventually develop into more mature cells or tissues in the shape of the scaffold. It is further envisioned that surfaces and compositions of the invention can be used to coat implantable devices, which may be structured or unstructured porous or solid surfaces. Said devices can deliver or recruit stem or progenitor cells to an area for purposes of repair or regeneration of tissues or cells. Stents for example can be coated with any of the surfaces or compositions of the invention to either repair or regenerate blood vessels. Stents coated with surfaces of the invention, e.g. NM23-S120G and to which stem or progenitor cells were attached could be implanted in a host or person to deliver cells or growth factors that stimulate the host's own cells. The methods can be carried out in vitro, ex vivo or in vivo.

Ligands

Ligands that promote binding of cells to the surface or that stimulate cellular proliferation can be attached directly to surfaces or indirectly, e.g. to polymers attached to surfaces. For example, antibodies that recognize cell surface receptors can be covalently attached to a polymer such as cyclodextrin or cyclodextran that has been attached or adsorbed onto a surface, see Examples 6, 10-12 and FIGS. 7, 10. Ligands that have some affinity for molecules on the cell surface are optionally attached to these surfaces to promote the attachment and growth of cells. The ligands may specifically bind to on the cell surface, such as growth factor receptors. Ligands may be proteins, peptides, small molecules, antibodies, polyclonal or monoclonal antibodies, bispecific antibodies, mono-valent or bi-valent antibodies, antibody derivatives such as Fabs, single chain antibodies, genetically engineered derivatives or derivatives in which the variable domain of an antibody is inserted into another protein such that it as able to specifically bind to its target. Alternatively, ligands need not have specific affinity for cell surface molecules. For example, ligands attached to the surface may cause cells to adhere to the surface through non-specific interaction. Non-specific interactions may be chemical or biological in nature. Surfaces derivatized with hydrophilic moieties such as hydroxyls or hydrophobic headgroups such as methyl groups may retain cells non-specifically via hydrophobic interaction. Surfaces bearing charged chemical or biological entities may adsorb cells through ionic interaction. Cells may additionally be captured by surfaces bearing entities that have some specificity for cells, including but not limited to RGD sequence containing peptides, poly-Lysine, positively or negatively charged surfaces, collagen, laminin, and other extracellular matrix components, including matrigel and matrigel-like substances. Cells can also be captured by other types of chemically modified surfaces. For example, surfaces coated with NTA-Ni and other metal chelates non-specifically bind cells and stem cells, see Example 15 and FIG. 12.

In a preferred embodiment, moieties that have specific affinity for molecules on the cell surface are attached to surfaces to facilitate the attachment of stem cells. For example, antibodies that bind to cell surface proteins that are specific markers of stem cells, such as SSEA3, SSEA4, or Tra 1-81 or Tra 1-60, are attached to surfaces. Stem cells adhere to these surfaces via the specific interaction between their cell surface proteins and their cognate antibody on the growth plate. Cells can then be cultured by either standard methods or novel methods of the invention that stimulate MUC1*, see Examples 1-4, 8-10, 12 and FIGS. 1-10. In another instance the ligand that is attached to the surface is a growth factor or a portion of a growth factor. In another instance, the ligand attached to the surface is an antibody, or a portion of an antibody that recognizes a cell surface molecule, which could be a growth factor receptor. In another instance, a ligand complex is attached to or immobilized on surfaces wherein at least one member of the complex has affinity for a cell surface molecule or provides the cell with an agent that modulates the cell's growth or differentiation. For example, protein G can be adsorbed onto, or specifically attached to, a surface via a histidine tag NTA-Ni interaction and an antibody that recognizes a stem cell surface marker is attached to the surface by its interaction with protein G, see Example 14, FIG. 11.

Mixed Surfaces

In some cases, it is desirable to have surfaces that present a mixture of ligands and components. These may be biological or chemical in nature or may be a mixture of biological and chemical components. For example, surfaces can be coated with a mixture of a growth factor, or equivalent activating antibody plus components of the extracellular matrix such as collagen or laminin. Surfaces coated with a mixture of laminin and growth factors or antibodies also promoted stem cell attachment and growth. For example, we have shown that surface coatings comprised of collagen or laminin and an antibody specific for a cell surface marker are useful for growing stem and stem-like cells.

In another example, laminin or collagen is mixed with a ligand of a cell surface marker. Experiments showed that mixing laminin with anti-MUC1* reduced the amount of antibody that was required for stem cell attachment and cell growth and normal stem cell colonies developed. In another aspect of the invention, mixed species are attached to a surface wherein one or more components are ligands that facilitate attachment of the cell to the surface and the other(s) is a component that provides the cell with an agent that affects the function of the cell. Examples of functional agents that can be attached to the surface include but are not limited to agents that promote growth, differentiation, or induce pluripotency.

Methods for Ligand Attachment

Ligands that promote cellular adhesion or are growth factors can be attached to surfaces in a variety of ways, including but not limited to covalent coupling, for example using EDC/NHS or maleimide coupling chemistries. Alternatively, ligands of the invention can be attached to surfaces via a non-covalent interaction or an affinity interaction. For example, ligands of the invention can be histidine tagged then attached to the surface via a nitrilo tri-acetic acid-nickel (NTA-Ni) moiety. Affinity tag interactions can be used to generate a growth surface suitable for culturing cells. For example, an NTA-Ni moiety is attached to a cell culture flask and a histidine tagged ligand is captured by NTA-Ni. The ligand either directly or indirectly binds to a cell surface receptor to anchor the cell to the surface. If the ligand is also a growth factor, then it serves to both cause cellular adhesion and promotes proliferation, see Example 14, FIG. 11.

In one embodiment, the ligand is Protein G or A to which is bound an antibody that recognizes a cell surface receptor, such as MUC1* or FGFR (fibroblast growth factor receptor). The Protein G or A can be non-specifically adsorbed onto a surface, covalently coupled or attached through an affinity tag-binding partner interaction. For example, cell culture flasks can be coated with an NTA-Ni moiety so that a histidine-tagged Protein G or A can be captured by the surface. An antibody to a cell surface receptor is then added, whereupon it binds to the Protein G or A that is immobilized on the surface.

In another aspect, ligands and agents that are attached to the surfaces can be attached to the surface in such a way that they can be released from the surface to change the local environment or so that the cell can consume the agent. Agents can be attached to the surface such that they are released from the surface as they degrade or they can be released in response to a stimulus. For example, agents can be attached to a surface using photo-sensitive or chemically sensitive linkers so that the agent can be released in response to light or via a chemical signal. Some linkers cleave in response to changes in pH. Genes or gene products, such as OCT4, NANOG, SOX2, KLF4 or NM23 that induce either pluripotency or genes or their products that induce differentiation, such as miR-145 (micro RNA) can be added to the media or attached to surfaces. They can be released from the surfaces by degradation over time or in response to a specific signal such as a specific wavelength of light to cleave the attachment bonds.

In a preferred embodiment, the ligand that is attached to or immobilized on the surface is a growth factor that recognizes a growth factor receptor on the cell surface. Antibodies that activate growth factor receptors on the cell surface can be attached to surfaces using any of the methods previously described or combinations thereof. In one instance, the growth factor is fibroblast growth factor (FGF) or basic fibroblast growth factor (bFGF) and the molecule on the cell surface for which the ligand has an affinity is the fibroblast growth factor receptor (FGFR). Alternatively, the ligand can be an antibody that recognizes FGFR. In another aspect of the invention, the growth factor is epidermal growth factor (EGF) and the molecule on the cell surface for which the ligand has an affinity is the epidermal growth factor receptor (EGFR). In another aspect, the affinity ligand is stem cell factor (SCF) or another agent, including an antibody, that activates c-Kit/SCF-R. Ligands that are attached to the growth surface can also be Flt 3 ligand, thrombopoetin (TPO), IL-2, IL-3, IL-n or antibodies that simulate their affect on their cognate receptors.

MUC1* Ligands

In a more preferred embodiment, the ligand attached to the growth surface has an affinity for the MUC1 cell surface protein. In a yet more preferred embodiment, the ligand has affinity for the PSMGFR portion (MUC1*) of the protein. And in a still more preferred embodiment, the ligand induces dimerization of MUC1*. In one instance the ligand is an anti-MUC1* antibody (Examples 1, 4, 7, 10, and FIGS. 1, 6A,B,D, 8. In another instance the ligand is NM23 or a variant such as S120G, or any other mutant or derivative that prefers dimer formation or functions as a dimer, see Examples 9, 12, 14, 15, 20 and FIGS. 9, 10, 11, 12 and 19. The surface may be configured such that NM23 is presented to the cell as a dimer. In another instance, the ligand attached to the growth surface is an antibody that binds to the extracellular domain of MUC1. Antibodies that bind to the portion of MUC1 that remains attached to the cell surface after the tandem repeat domain is cleaved and shed from the cell surface are preferred. For example, bivalent antibodies that bind to the PSMGFR sequence of MUC1 activate the growth factor receptor function of cleaved MUC1 and stimulate cell proliferation. Polyclonal or monoclonal antibodies generated by immunization with at least a portion of the PSMGFR peptide are attached to the surfaces to both promote the attachment of cells to the surface and to stimulate growth of the cells via activation of the MUC1* growth factor receptor.

Either polyclonal or monoclonal antibodies, as well as both natural and non-natural antibody derivatives, can be generated or selected such that they are better suited for stem cell adhesion than antibodies generated with, or selected for affinity to, the entire PSMGFR sequence. Polyclonal antibodies generated by immunizing with rabbits with a peptide corresponding to the sequence of the MUC1* extra cellular domain but with the 10 amino acids proximal to the cell surface deleted, "C-10 PSMGFR" generated antibodies that were more efficient in promoting stem cell adhesion than antibodies generated against either the full PSMGFR peptide or an "N-10 PSMGFR" (QFNQYKTEAASRYNLTISDVSVSD-VPFPFSAQSGA) (SEQ ID NO:3), that had the most distal 10 amino acids deleted, see Example 16 and FIGS. 13, 14. Antibodies that have improved ability to bind stem cells can also be isolated from polyclonals raised against the full PSMGFR peptide by affinity purifying them over surfaces that present the C-10 PSMGFR peptide or other N-terminal fragment.

Figure 13:
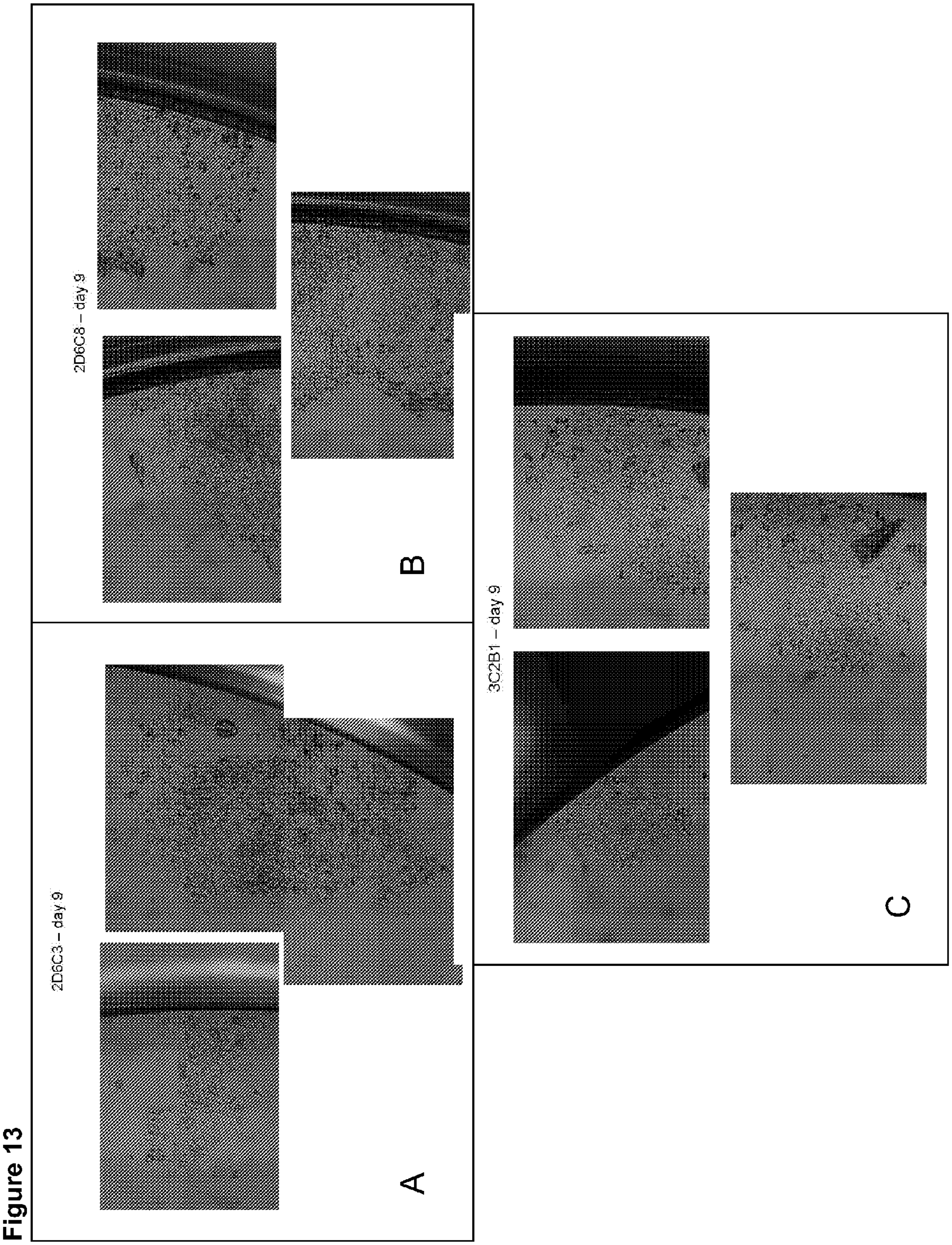
FIGS. 13A-13C show photos of hu BG01v/hOG ES cells growing on adsorbed supernatant from hybridoma clones each secreting a different monoclonal antibody. Monoclonal antibodies that best enable stem cell adhesion are identified in this way.
Figure 14:
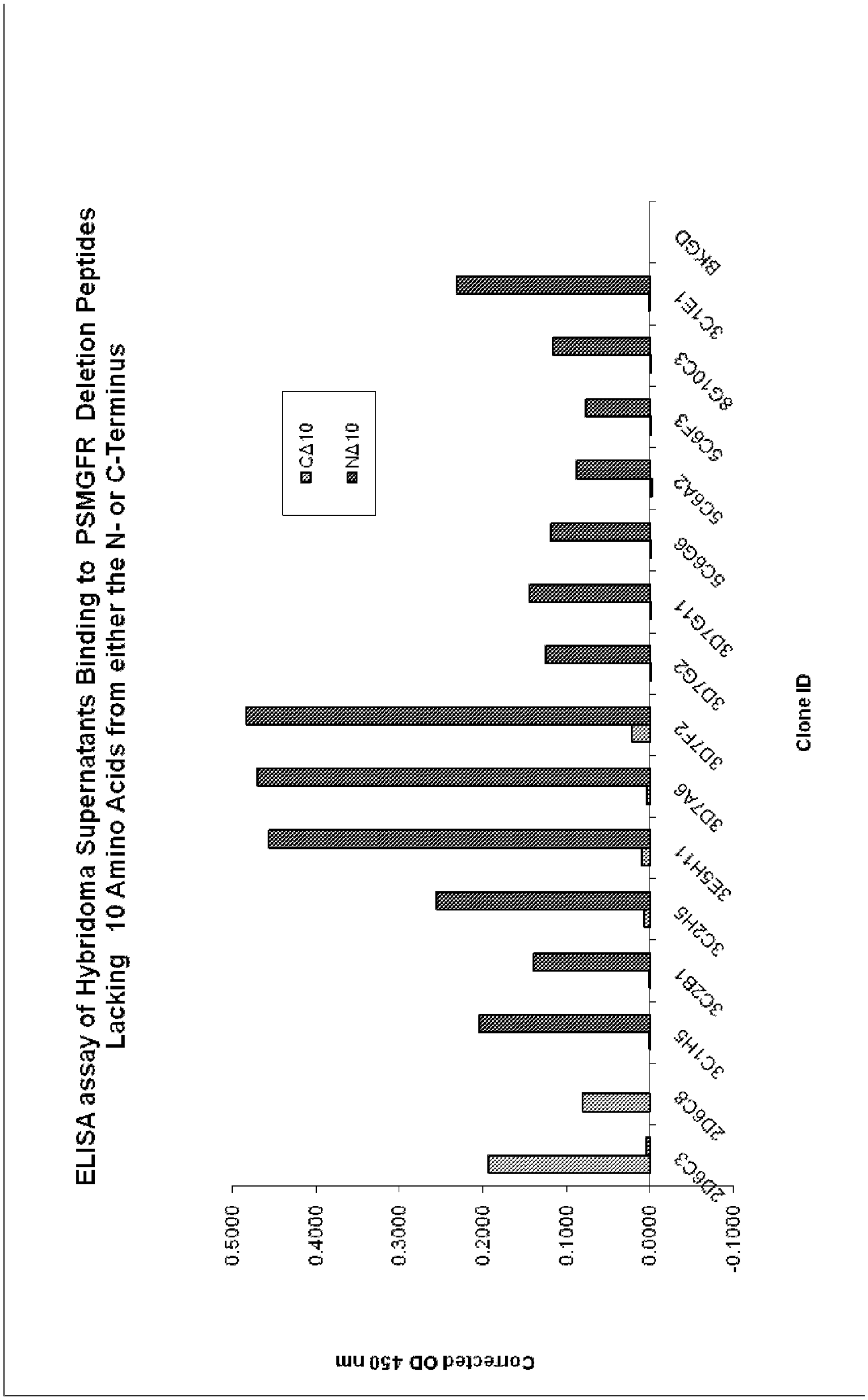
FIG. 14 is a graph of an ELISA assay in which hybridoma supernatants were tested for their ability to bind to deletion mutations of the PSMGFR peptide that were missing 10 amino acids from either the N- or C-terminus. The hybridomas that enabled stem cell attachment to a surface coated with their supernatant, also showed binding to the C-10 PSMGFR peptide (GTINVHDVETQFNQYKTEAASRYNLTISDVSVSDV). We reasoned that antibodies that bound to the more distal portions of the MUC1* extra cellular domain would better enable stem cell attachment to surfaces.

Hybridoma clones that secreted a monoclonal antibody that bound to the C-10 PSMGFR peptide but not the N-10 PSMGFR peptide were shown to facilitate stem cell adhesion to surfaces, see FIGS. 13 A-C, FIG. 14. In contrast, monoclonal antibodies that bound to N-10 PSMGFR peptides but not to the C-10 PSMGFR peptides barely enabled stem cell adhesion. Both monoclonal antibody types were able to stimulate cell growth when they were added to the culture media.

In a preferred embodiment, stem cells are cultured over a surface that presents NM23 which is a ligand of the MUC1* growth factor receptor. NM23 can be directly or indirectly attached to surfaces. In one aspect of the invention, NM23 or the S120G mutant that prefers dimerization are non-specifically adsorbed onto surfaces for cell growth, see Example 15, FIG. 12. In another aspect of the invention, a surface is first derivatized with an affinity tag binding partner such as NTA-Ni that binds to histidine-tagged proteins or peptides. Histidine-tagged NM23 is then non-covalently coupled to the NTA-Ni surface. MUC1*-positive cells such as stem cells and some progenitors are then added to the NM23 surfaces, whereupon the cells adhere to the surfaces and grow. In a still more preferred embodiment, NM23 S120G mutant is covalently coupled to cyclodextran.

Methods for Harvesting

In another aspect of the invention, novel methods for harvesting cells from surfaces of the invention are described. The invention includes these harvesting methods that are useful for surfaces of the present invention as well as for many other cell growth systems. The invention also includes the use of standard harvesting methods, such as manual dissection and enzymatic cleavage, with the novel surfaces of the invention. Some of the cell harvesting methods depend on the identity of the surface components. For example, cells growing by adsorption onto antibody surfaces can be released by the addition of excess peptide having the same sequence as the antibody epitope. For example, if the antibody recognizes the extracellular domain of MUC1*, then the cells can be released by adding an excess of a peptide having some or all of the sequence of the extracellular domain of MUC1*. The free peptide competes with the MUC1* receptor on the cells for binding to the surface attached antibody. Binding of the peptide to the antibody releases the cell, see Example 4, FIG. 6D. Cells cultured on surfaces presenting antibodies that are attached to a surface by binding to Protein G or A are released from the surface by adding excess Fc portions or an excess of an irrelevant antibody. Since Protein G binds to Fc domains, free Fc competes with the cognate antibody for binding to the surface-attached Protein G or A and releases the antibody-complexed cells. Cells cultured on surfaces with ligands attached by an affinity tag-binding partner interaction are released by adding an agent that interferes with the affinity tag-binding partner interaction or by adding an excess of the portion of the affinity tag that interacts with the binding partner. For example, cells growing on histidine-tagged ligands bound to NTA-Ni surfaces are released by adding either imidazole, an irrelevant histidine peptide, or an excess of at least a portion of the binding partner of the surface attached ligand. In the case of NM23 surfaces, cells can be released by adding an excess of a peptide having a sequence essentially the same as at least a portion of the extracellular domain of MUC1*, such that addition of the excess peptide competes with the MUC1* cell surface receptor for binding to the surface attached NM23, thus releasing the cells. Alternatively, NM23 is made with an affinity tag that facilitates attachment to a surface. Strategies that interfere with the interaction between the affinity tag and the surface release the NM23 and the attached cell from the surface. Similarly, His-tagged Protein G (plus an antibody) or His-tagged NM23 can be released from the surface by adding: a) imidazole (at 0.5M); or b) excess of $(His)_6$ peptide.

Any affinity tag, binding partner pair can be used for the attachment of ligands to the surface and interruption of the affinity tag binding partner interaction will release the stem cells from the surface. Examples of suitable affinity tag, binding partners pairs include but are not limited to NTA-Ni/histidine tag, glutathione/GST fusion, maltose/maltose binding protein and biotin/streptavidin.

Growth Media

The surfaces and harvest methods described herein are compatible with standard stem cell culture methods as well as novel methods. The standard stem cell culture media requires the addition of exogenous basic fibroblast growth factor (bFGF) and growth over fibroblast feeder cells because stem cell growth until now has required as yet unidentified growth factors that are secreted by these cells. Stem cells can also be grown over matrigel according to standard protocol, except that in addition to bFGF, conditioned media from fibroblast feeder cells (CM) must be added to roughly 30-50% of the media. Inactivated human foreskin (HS27) fibroblast feeder cells are typically used for the growth of embryonic stem cells.

Figure 4:
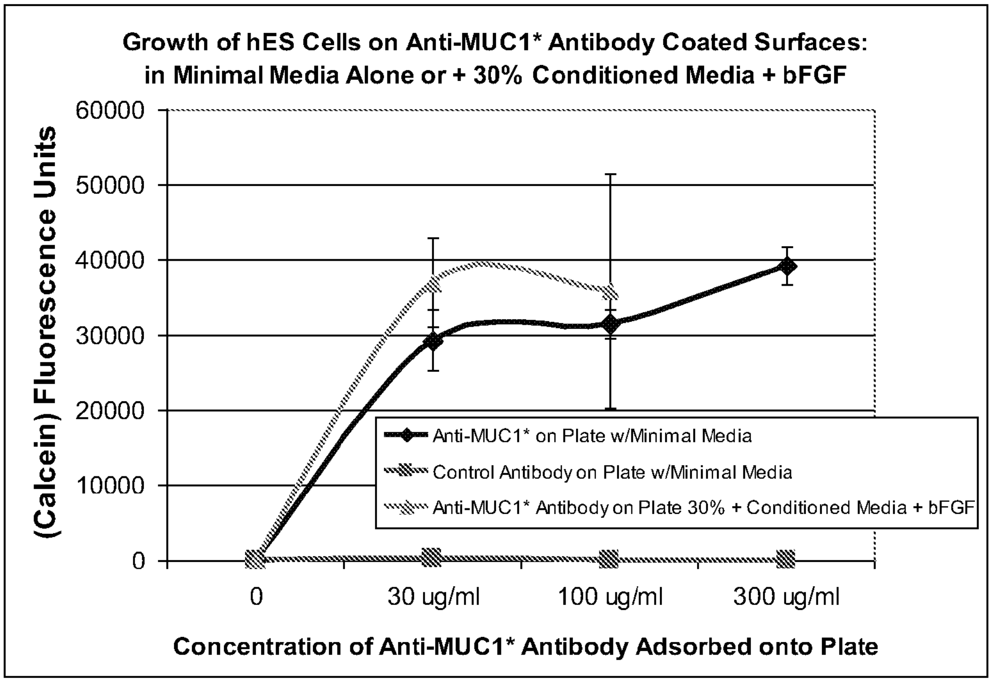
FIG. 4 shows that surfaces coated with anti-MUC1* antibody supports stem cell growth whether cultured in minimal stem cell media alone or bFGF plus conditioned media from fibroblast feeder cells. An irrelevant antibody coated onto a different surface did not cause stem cell adhesion and cells died within 24 hours.
Figure 5:
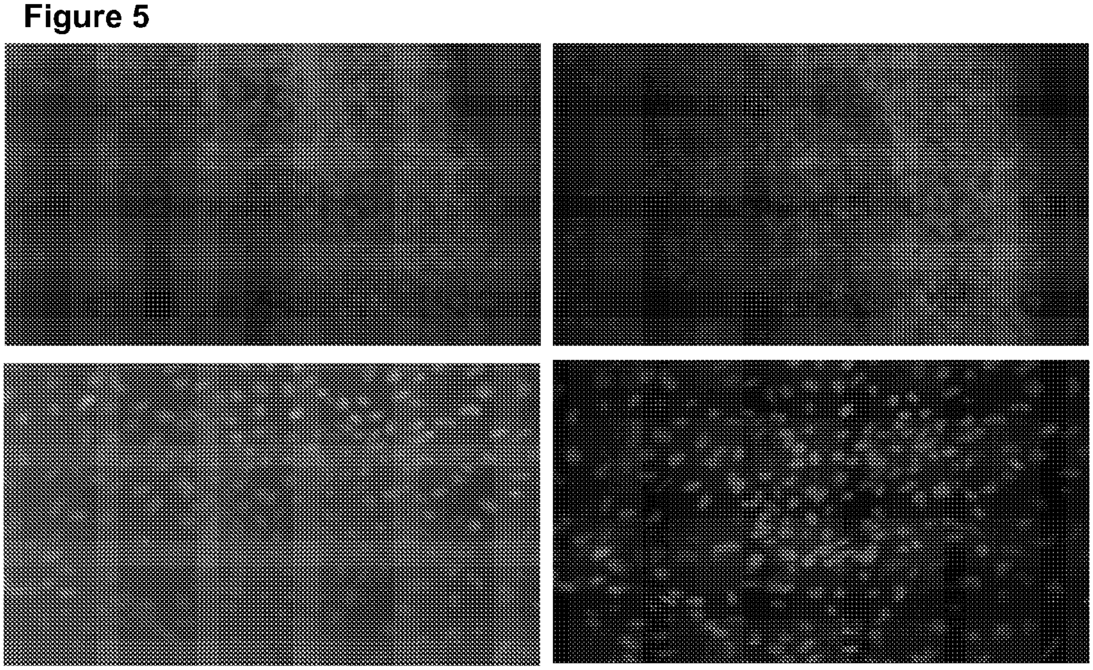
FIG. 5 shows photos of human stem cells attached to matrigel after multiple passages in culture containing only anti-MUC1* and minimal media. The photos on the left show DAPI staining the nuclei of all the cells and the panels to the right show a 1:1 correlation to OCT4 staining. Together they show that all the cells remain OCT4+, which indicates pluripotency.
Figure 6:
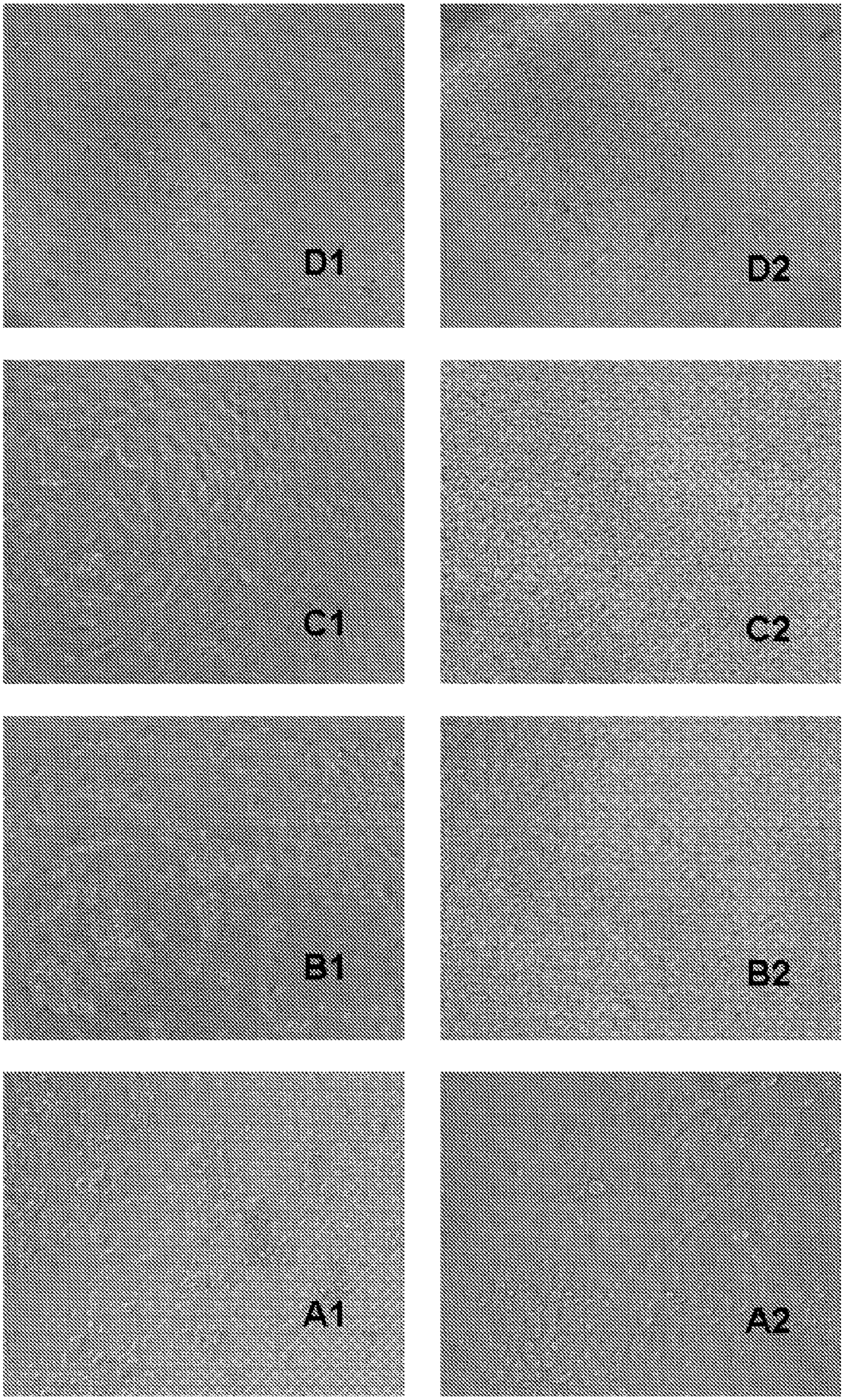

We have demonstrated that standard growth media are compatible with growth over surfaces of the invention, Example 4, FIG. 6C and Example 3, FIG. 4. Like growth over matrigel, bFGF mediated growth also requires fibroblast conditioned media to support stem cell growth on the inventive surfaces described herein. Preferred are culture media containing MUC1* stimulators or dimerizing agents. Either antibodies that recognize the PSMGFR peptide; or NM23, wild type or mutant S120G, are preferred growth factors and can substitute for bFGF and fibroblast conditioned media, see FIGS. 6, 9, 10, 11 and 12. The growth of human embryonic stem cells, attached to Matrigel, Cell Start (Invitrogen), Geltrex (Invitrogen) or any of the surfaces of the invention is consistently better when either anti-MUC1* antibodies or NM23-S120G is added to minimal stem cell media in place of bFGF and HS27 conditioned media; growth rate, colony morphology and inhibition of differentiation is consistently better when MUC1* stimulators replace bFGF plus conditioned medium (CM).

Conditioned media collected from growing MUC1*-positive cancer cells increases stem cell growth and colony formation, while inhibiting differentiation. Human stem cells growing on matrigel, NTA-Ni, anti-MUC1* antibodies or NM23 surfaces were cultured in minimal stem cell media plus conditioned media collected from growing MUC1*-positive cancer cells. Conditioned media from T47D cells, which are MUC1*-positive breast cancer cells, when added to NM23-S120G, or anti-MUC1* antibodies or bFGF greatly improved stem cell growth, colony formation and inhibition of differentiation compared to conditioned media from HS27 fibroblast feeder cells, see Examples 14, 15, and FIGS. 11, 12. The surfaces and harvest methods described herein can be used for cells other than stem cells.

Anti-MUC1* Antibodies for Cell Sorting

Purification:

Pure populations of pluripotent stem cells can be purified from mixed populations of cells. Massive stem cell growth may generate some stem cells that have spontaneously differentiated. Therefore, high throughout methods for capturing the desired pluripotent cells and disgarding the differentiated ones may be necessary. MUC1* is a cell surface marker for pluripotency that is lost before OCT4 when cells initiate differentiation. Pure populations of pluripotent (MUC1*-positive) stem cells can be isolated from mixed populations by capturing them on a column derivatized with anti-MUC1* antibody. Conversely, the MUC1* affinity column will be used to remove MUC1*-positive cells from differentiated cells prior to transplantation to reduce the risk of teratoma formation.

Figure 15:
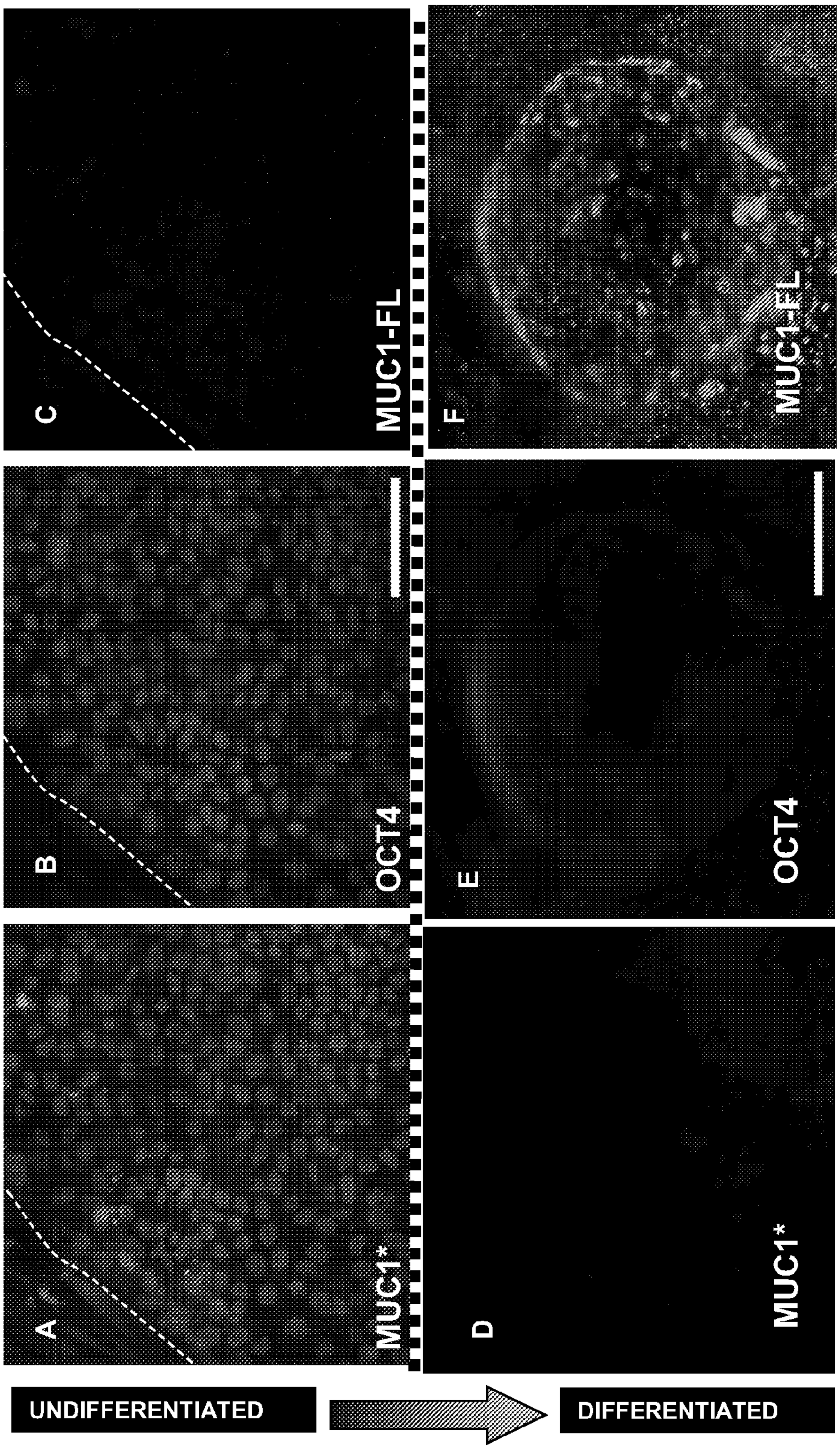
FIGS. 15A-15L show photos of ICC staining of H9 human embryonic stem cells before and after they began to differentiate. Anti-MUC1* stained all cells of undifferentiated colonies and co-localized with OCT4, which is the gold standard indicator of pluripotency (FIG. 15A, 15B). VU4H5 antibody that identifies MUC1-full-length did not stain any of the undifferentiated cells.
Figure 15:
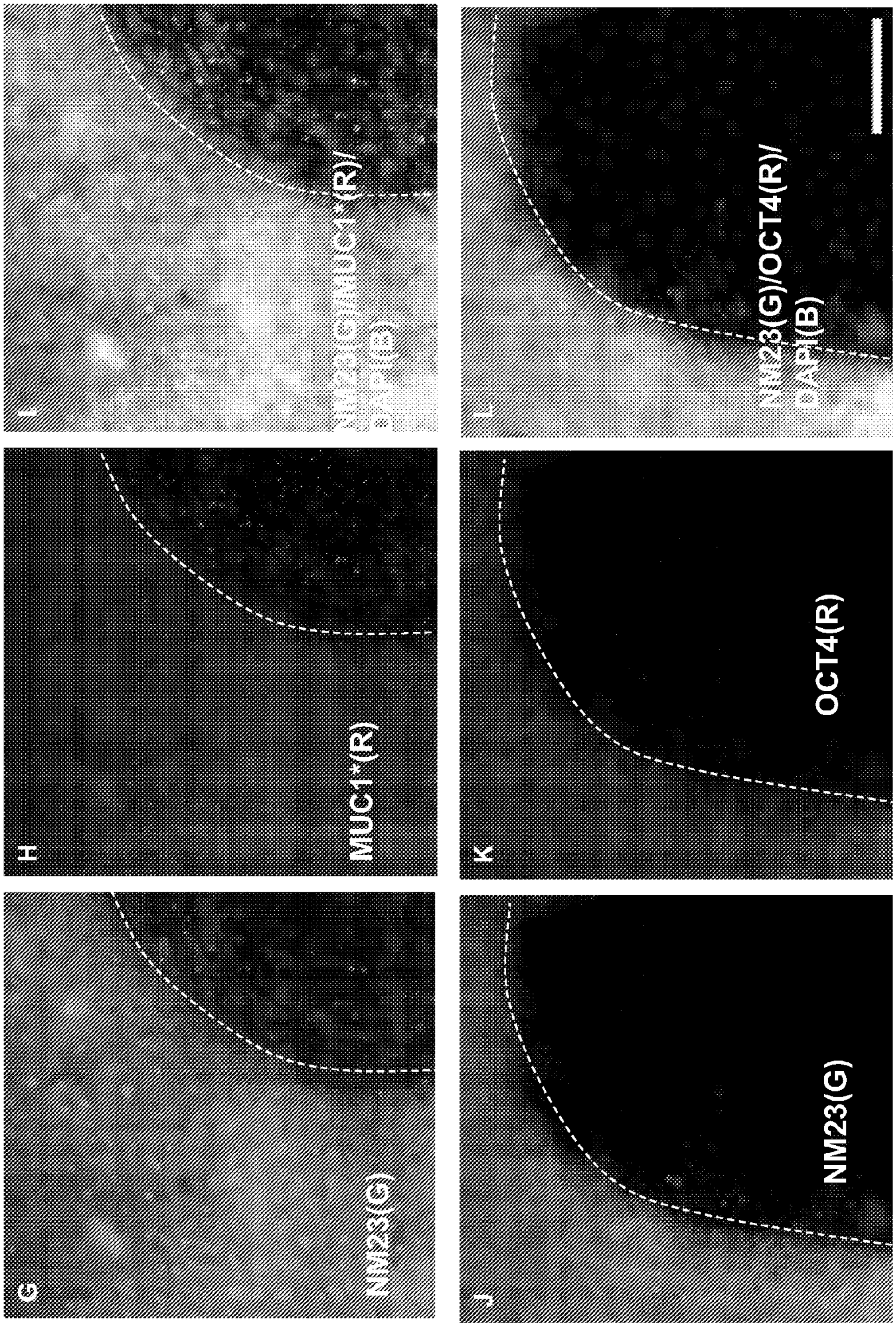

In many cases, it is desirable to separate stem and progenitor cells according to their stage of differentiation. We previously showed that pluripotent stem cells present the clipped, MUC1* form and not the full-length MUC1 protein; after differentiation begins, MUC1 cleavage stops and the cells are mostly MUC1* negative and positive for the full-length form. Many antibodies are available that bind to the tandem repeat units of full-length MUC1, e.g. commercially available VU4H5 or HMPV antibodies. Cleavage of MUC1 to the growth factor receptor form, MUC1*, releases these portions from the cell surface, so antibodies against the tandem repeats would not stain MUC1*. Although the PSMGFR sequence is present in both MUC1 and its clipped form (MUC1*), antibodies against the PSMGFR sequence do not bind to the full-length MUC1 because the epitope is masked. FIG. 15 A-L shows photos of immuno-cytochemical (ICC) staining of H9 human embryonic stem cells before and then after they began to differentiate. A rabbit polyclonal antibody raised against the full PSMGFR peptide stained virtually every cell of an undifferentiated colony. OCT4, which is the gold standard indicator of pluripotency for stem cells exactly co-localized with the anti-MUC1* (also called anti-PSMGFR) antibody staining, FIG. 15 A,B. the VU4H5 antibody that binds to the distal tandem repeats of MUC1-full-length did not stain any of the undifferentiated cells, FIG. 15 C. However, when these same cells were allowed to differentiate by withholding bFGF for 14 days, the reverse MUC1 pattern was observed. No MUC1* staining or OCT4 staining was observed, FIG. 15 D,E, but every cell stained positive for the full-length MUC1, FIG. 15 F. Similarly, undifferentiated stem cells stained positive for NM23, the ligand of MUC1* and NM23 exactly co-localized with MUC1*, FIG. 15 G-I and OCT4, FIG. 15 J-L. Cleavage enzymes MMP14, MMP16, and ADAM-17 have been implicated in the cleavage of MUC1. They also co-localize with MUC1* on undifferentiated stem cells, Hikita et al, PLoS ONE, 2008.

Consequently, anti-MUC1* antibodies optionally in combination with others including antibodies against NM23, MMP14, MMP16, ADAM-17 and OCT4 can be used to identify and isolate pluripotent stem cells from a mixed pool. Antibodies against SSEA3/4 or Tra 1-81/1-60 may also be used in conjunction with anti-MUC1* antibodies to identify pluripotent stem cells. Pools of undifferentiated and differentiated stem cells can be stained with antibodies that bind to the PSMGFR peptide and antibodies that bind to the portion of MUC1 that is released when it is clipped. Standard cell separation methods such as FACS (fluorescence activated cell sorting) can then be used to separate out MUC1* presenting cells from those that present the full-length form of the protein. In some cases, it is desirable to remove those stem cells that have differentiated from those that remain pluripotent. In other cases, it is desirable to remove those stem cells that remain pluripotent (MUC1*-positive) because those could increase the risk of teratoma formation if transplanted into a host. Combinations of anti-MUC1* antibodies, i.e. anti-PSMGFR antibodies and NM23 antibodies can also be used to identify pluripotent stem cells and also to identify those progenitor cells that can be expanded by MUC1* stimulation.

Cancer Stem Cells Sorting Depleting

Cancer cells increase expression of MUC1*, but not MUC1-full-length, when they acquire resistance to chemotherapy drugs. These cells that are resistant to chemotherapy are also called cancer stem cells. Therefore, anti-MUC1* antibodies optionally combined with other antibodies including antibodies against NM23, MMP14, MMP16, ADAM-17 and OCT4, can be used to identify cancer stem cells. In one embodiment of the invention, anti-MUC1* antibodies and combinations of these other antibodies are used to deplete cancer stem cells from a patient, for example, from a patient's blood.

FACS and Growth of Human Stem Cells

The present invention further discloses using anti-MUC1* antibodies; or NM23 or NM23 S120G or other mutants that prefer dimerization to stimulate the growth of and inhibit the differentiation of progenitor cells that express the clipped form of MUC1 (MUC1*). Although MUC1 cleavage is turned off when stem cells initiate differentiation, cleavage resumes at later stages. Hematopoietic stem cells (HSCs) for example, express the clipped form, MUC1* and can be made to proliferate by exposing the cells to MUC1* dimerizing agents. Hematopoietic stem cells are CD34-positive and CD38-negative when they are considered stem cells. When they progress to the next stage of differentiation, they become CD34-positive and CD38-positive. We obtained human HSCs from cord blood and cultured them in minimal stem cell media plus anti-MUC1* antibodies at varying concentrations. Cells were cultured for 11 days with fresh antibodies added on day 5 post-plating. Cells were analyzed and sorted by FACS. FIGS. 16A and B, Example 18 shows that the number of cells that remained hematopoietic stem cells, CD34+/CD38−, increased with increasing anti-MUC1* concentration. Conversely, the number of cells that had progressed to the next progenitor stage, CD34+/CD38+ increased as the concentration of anti-MUC1* decreased. These results show that stimulation of MUC1* growth factor receptor inhibited differentiation of HSCs.

Figure 17:
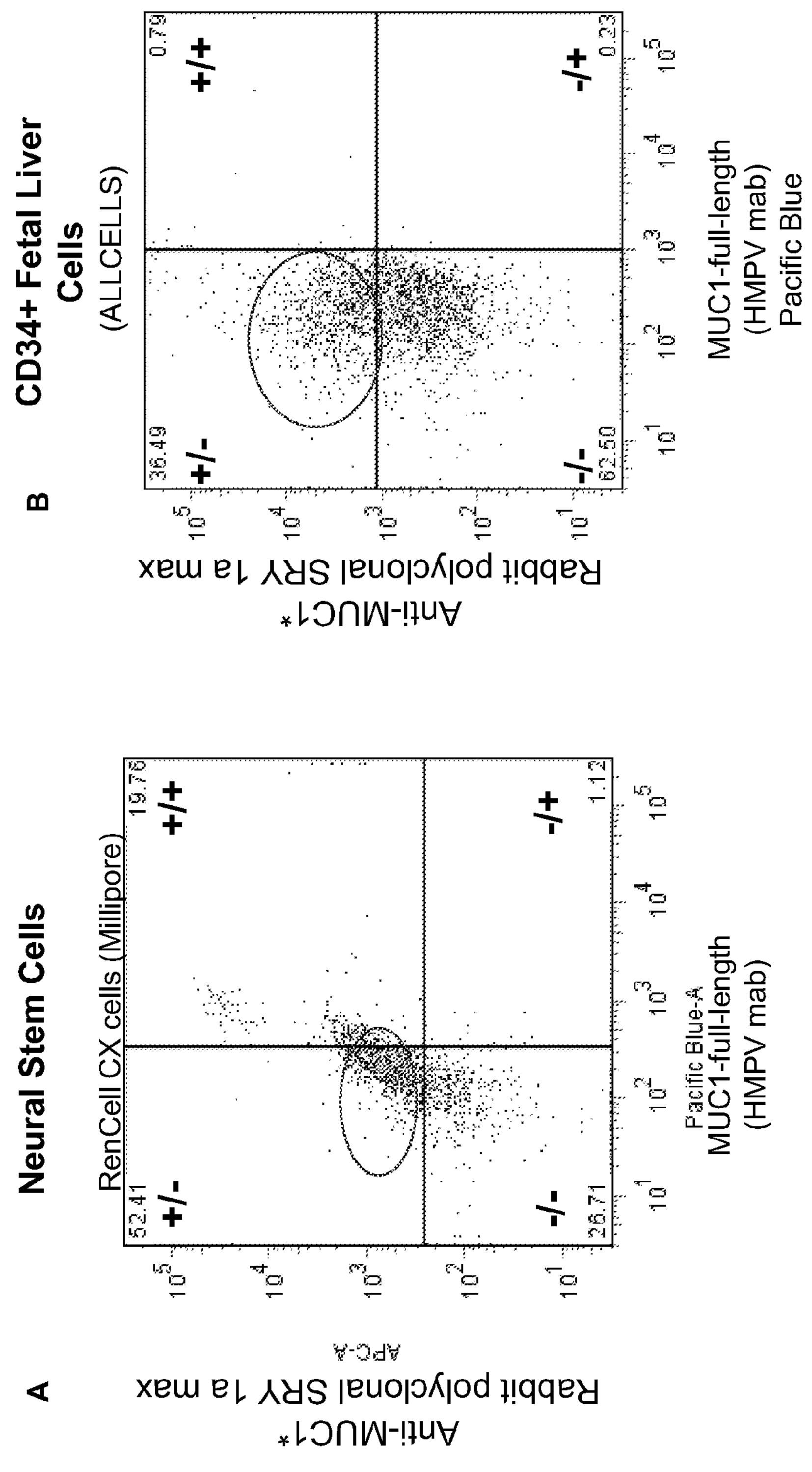
FIGS. 17A-17B show FACS scans of neural stem cells (A) and fetal liver cells (B). Cells were obtained from the vendor and immediately stained with both a fluorescently labeled anti-MUC1* antibody and a labeled antibody (HPMV) that recognizes the distal portion of full-length MUC1. The FACS scans show MUC1 is mostly clipped to MUC1* on both types of early progenitors. Subsequent experiments showed that anti-MUC1* stimulated the growth of both types of cells in a concentration dependent manner.
Figure 18:
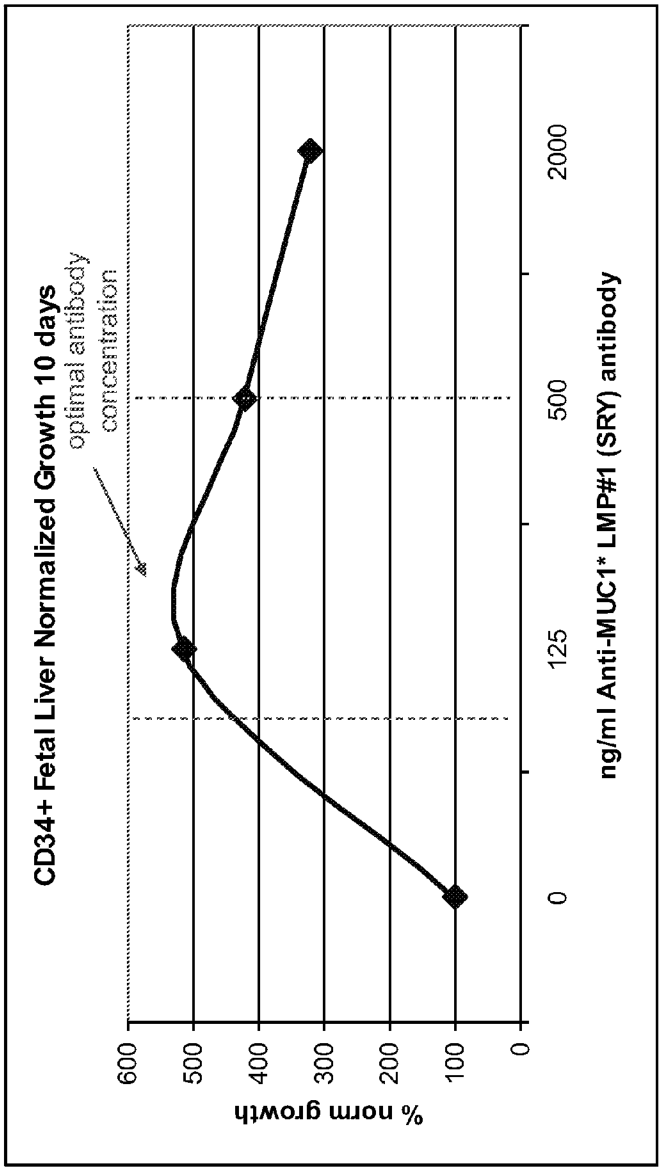
FIG. 18 is a plot of the growth of fetal liver cells as a function of anti-MUC1* concentration that shows that MUC1* progenitor cells can be isolated and expanded by stimulating the MUC1* receptor.

Hematopoiesis occurs in the liver of the fetus and in early life. Human fetal liver cells were FACS sorted using an antibody that binds to the PSMGFR sequence of the MUC1* extra cellular domain and VU4H5 which is a commercially available antibody that binds to the tandem repeat units of full-length MUC1. The FACS scan of FIG. 17B shows that fetal liver cells are mostly MUC1*-positive and full-length-negative. MUC1*-positive fetal liver cells were isolated and expanded by growing them in minimal media plus anti-MUC1* antibodies. The graph of FIG. 18 shows that the growth of fetal liver cells is greatly increased at optimal anti-MUC1* antibody concentration. The growth declines when the antibody goes to excess and there is one antibody attached to each receptor rather than one antibody binding to each two receptors. Similarly, undifferentiated stem cells can be separated from those that have differentiated by performing FACS or other separation technologies using binding agents such as antibodies that bind to the PSMGFR region or the distal portion of the full-length MUC1 protein.

Other types of cells may present the clipped form of MUC1 and can be isolated or depleted from cell populations on the basis of whether or not antibodies that recognize the PSMGFR portion of the MUC1 protein bind to the cells.

Capture, Growth, Release, Sorting Combined

In some cases it may be desirable to separate one cell type from another before, during or after a growth period. In one method each spatial address of a surface presents a different ligand, each of which has affinity for a different cell type or for specific markers that identify a cell stage or type. Cells are added to the surface and by affinity interaction the cells become spatially separated according to markers on the surfaces of each cell type. Separated cells can be individually harvested for culturing in separate locations or can be cultured as a mixture then harvested later by location. In one method, different modes of attachment are used to attach different marker-specific ligands. For example, at one location, ligands to MUC1*, a marker for pluripotent cells, are attached to a surface by histidine-tag/NTA-Ni interaction, while at another location, antibodies to a marker for cells differentiating along the ectoderm line, are attached to the surface by a Protein G. In this way, the undifferentiated cells are released by addition of imidzole and the ectoderm cells are released by the addition of excess Fc. In another method, the two or more surfaces that each present a different affinity ligand are housed in separate locations. The two or more surfaces may be connected by flow channels. In one embodiment, a mixture of cells is introduced to a first surface that captures cells that express the cognate molecule for the ligand that the surface presents. The supernatant or flow through is then introduced to a second surface that captures the cells that present the cognate cell surface molecule that facilitates binding to its surface. The supernatant or flow through is then introduced to a third surface and so on such that the desired cell types are captured by spatially addressable surfaces. This method is used to separate cells by type or to separate, then grow the cells. Flow channels and valves can be used such that flow is allowed during the period of cell separation but then limited so that cells of a specific type can be cultured under conditions that are optimal for that particular cell type.

Methods of the invention are suitable for the separation of cells that may undergo differentiation during the growth process. Systems comprised of mixed surfaces that each present an affinity ligand for a particular differentiation state marker or cell type are used in a dynamic system to sort progeny as a function of differentiation state. Cells initially attach to a first surface by interaction of one of their cell surface proteins that is a marker of an initial differentiation state, which is no longer expressed by the cell or its progeny in another state of differentiation. The cell would therefore be released wherein it would migrate to a new location that presents a ligand with affinity for a cell surface marker that defines its new differentiation state. This sorting can take place geographically e.g. location in a flow channel, introduction of supernatant to a new surface, or self-sorting where cells are released from one location (can be a particle) and migrate to a second location (can be a neighboring particle) where an affinity ligand for a different cell marker is immobilized. In one embodiment, beads or particles that display different affinity ligands are mixed together and cells attach to the bead/particle for which they present the cognate molecule on their surface. In this case beads or particles also possess a property that allows them to be sorted after cellular attachment. For example, magnetic beads that present a ligand(s) with affinity for CD34+/38− hematopoietic stem cells are mixed with non-magnetic beads that present ligand(s) with affinity for CD34+/CD38+ progenitor cells. After cell culturing, beads bearing CD34+/38− cells are magnetically isolated and collected, while the remaining beads comprise the population of CD34+/38+ cells. Alternatively, spatial locations, beads or particles can have attached thereto moieties that can be captured by other surfaces for purification. As an example, beads that present an affinity ligand and a purification ligand will capture all the desired cell types via the interaction between the affinity ligand and cognate cell surface receptors; the purification ligand will attach the beads to a specific spatial address via binding between the purification ligand and a moiety on a second surface. The invention includes using this method to sort cells from a mixed pool wherein the cells are in various stages of differentiation. The invention also includes the use of this method for sorting cells in cell culture situations wherein cells are being induced to be pluripotent and it is desirable to select and amplify those cells that have certain stem-like properties at various times during the process of inducing pluripotency.

In an alternative method, cells are separated by immobilization onto particles that present ligands that are specific for different cell types. A mixture of cells is introduced to a mixture of particles. Cells separate onto particles that present the ligand that has affinity for its cell surface molecule. Particle-bearing cells can then be separated prior to culturing or cultured all together then separated after a growth period. Cell-bearing particles are separated by a variety of means based on the properties of the particle itself or properties of ligands attached to the particles. For example, particles can be separated based on size, charge, density, optical properties, electromagnetic properties and the like. These properties can be inherent properties of the particle itself or properties of an attached ligand. For example, the particles themselves may be fluorescent or ligands attached to the particles may be fluorescent. Particles are easily separated by properties including but not limited to magnetic, charged, fluorescent or electronic characteristics. Alternatively, particles can be used that present ligands that bear a second affinity ligand. In this case, in addition to bearing a ligand that facilitates the attachment of a cell, the particle would also bear a moiety that facilitates the attachment of the cell-bearing particle to a separate surface or location.

In another aspect of the invention, one surface presents two or more different ligands that have different functionalities. In some cases, the two or more ligands are more selective than a single ligand for the attachment of specific cells. In another case, a first ligand mediates the attachment of cells while the second ligand targets the cell/surface complex to a specific location that may be another surface or another location. In this way, surfaces that are articles or particles that bear ligands that capture a specific cell type can be purified away from non-target cells via attachment to a second surface or location. In other cases, it may be desirable to capture two or more different cell types yet have the ability to separate the cells, according to type, either before, after or during a growth period. This is accomplished by using surfaces or particles that present a first ligand that facilitates attachment of a specific cell type and a second ligand that targets the surface to a specific location. The targeting ligand may be a chemical or biological moiety that targets the particle by binding to an entity at a different location. Alternatively, the targeting ligand may be an entity that imparts certain properties to the particle that make it separable from other particles. For example, the ligand may be a fluorescent moiety, a dye, a charged moiety, or a moiety with optical or electromagnetic properties. In another aspect of the invention, the targeting ligand is not a ligand per se but rather is a specific property of the particle.

Surfaces and novel growth factors of the invention are envisioned to be used for the growth of stem, progenitor and other MUC1*-positive cells in a variety of formats, including but not limited to wave bags, roller bottles, growth in suspension, and for use in any type of containment vessel including a live host. The containment vessel may be maintained in motion to prevent the adhesion of cells to the vessel. The interactions between surface-immobilized ligands and their cognate targets on cells allow for exchange of media without loss of cells. When it is desired to harvest or deplete cells, surfaces which may be particles, can be isolated by centrifugation, gravity, electromagnetic or electric field. Agents can be added to release the cells from the surfaces. Excess affinity ligands can be added free in solution so that they compete for binding to the receptors on the cell surface and thus release the cells from the particles. In one embodiment, if the affinity ligand is an antibody, excess Fc portions of antibodies are added that serve to release the antibody from the particle and cell plus activating ligand are free in solution. In another embodiment, the ligand is NM23 or a mutant thereof.

The present invention further discloses using NM23 wild type or mutants that prefer formation of tetramers and hexamers to induce the differentiation of stem cells, progenitors or cells that have been induced to be stem-like through the introduction of nucleic acids, siRNAs, micro RNAs or proteins.

The invention also includes methods for inducing the differentiation of stem cells and stem-like cells. Ligands that block the interaction of MUC1* and its dimerizing ligands induce differentiation. For example, the addition of a peptide containing enough of the sequence of the extracellular domain of MUC1* to block the interaction of NM23 and MUC1* extracellular domain induces differentiation. Similarly, the addition of low concentrations of an Fab (monovalent) of an anti-MUC1* antibody prevents receptor dimerization, which promotes pluripotency, and results in initiation of differentiation. The MUC1* extra cellular domain peptide or the Fab of antibodies that bind to MUC1* can be added to culture media or attached to surfaces. Stem cells can be harvested then replated over surfaces presenting ligands such as the MUC1* extra cellular domain peptide of the anti-MUC1* Fab to induce differentiation. Micro RNA 145 (miR-145) suppresses MUC1 and in so doing induces differentiation. miR-145 can be added to stem and progenitors in culture to promote differentiation. In contrast, inhibitors of miR-145, such as siRNA specific for miR-145, can be added to growing stem and stem-like cells to inhibit their differentiation.

Ligand-Polymer Growth Surfaces:

The attachment of ligands of the invention to polymers or macromolecules, such as dextrin or cyclodextran greatly improves their ability to capture and grow the targeted stem and progenitor cells. The resultant surfaces simulate ligands in solution. The covalent attachment of both proteins and antibodies to cyclodextran increased cellular adhesion greatly decreased the amount of ligand required, compared to when the ligand was directly adsorbed onto the surface. Ligands such as NM23 or anti-MUC1* that were coupled to cyclodextran supported embryonic stem cell growth in minimal media without the need for additional growth factors in the media. Antibodies and cognate proteins like anti-MUC1* and NM23 can also be attached to other polymers and other surfaces including porous membranes and scaffolds. The invention includes both structured and un-structured surfaces. For example, stents, artificial structures such as ears, can be coated with biological and/or chemical agents that facilitate the attachment of stem and progenitor cells. These ligands may optionally provide the stem or progenitor cells with nutrients or signals that influence their growth and/or differentiation.

Synthetic Antibody Growth Surfaces:

The invention also contemplates the use of synthetic ligands as growth factors for cell growth media and also for surface coatings that facilitate the attachment of cells. For example, small molecules that bind to cell surface proteins are readily identified using standard screening methods. The inventors previously disclosed small molecules that bind to the MUC1* extra cellular domain, and to the PSMGFR peptide in particular. These synthetic molecules can then be non-covalently or covalently attached to surfaces for the adsorption and growth of non-adherent cells, such as stem cells, iPS cells and early progenitors like hematopoietic stem cells that express MUC1*. If the synthetic ligands bind to growth factor receptors that are activated via dimerization, then activating dimers of the small molecules can be made by covalently linking two small molecules to make dimers. In a preferred embodiment, the small molecules bind to the PSMGFR peptide and the small molecules are linked so that they become dimers and function as artificial growth factors. In another aspect of the invention, small molecule monomers can be attached to a surface so that they are close enough together that they behave like a dimer. That is to say, the surface acts as the linker, so that the small molecules are presented to the cell surface receptor in a defined geometry that activates the receptor. These small molecule dimers can be used in the same ways as the natural growth factors, including that they can be added to growth media as well as adsorbed or covalently attached to surfaces. Synthetic surfaces would be: a) cheaper to manufacture; b) amenable to long-term storage; and c) immune to degradation. The inventors previously described small molecules that bind to the extracellular domain of MUC1* with high affinity. Small molecule dimers (bivalent) that mimic anti-MUC1* antibodies are synthesized by coupling of the small molecules to a linker. Synthetic antibodies can be immobilized either directly onto plate surfaces or via a polymer coating.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Pluripotent Stem Cells Attached to Matrigel and Cultured in Minimal Media Plus Anti-MUC1* Antibodies Proliferate Faster and with Less Differentiation than Growth Supplemented by bFGF and Conditioned Media from Fibroblast Feeder Cells H9 hESCs (WiCell) or BG01v/hOG, (Invitrogen) were cultured at 37° C. and 5% $CO_2$ on either mitomycin-C inactivated Hs27 human foreskin fibroblasts (ATCC) in 6 well plates (BD Falcon). hESC culture media consisted of DMEM/F12/GlutaMAX I with 20% Knockout Serum Replacement, 1% non-essential amino acids stock, 0.1 mM β-mercaptoethanol (all from Invitrogen) and 4 ng/ml human basic fibroblastic growth factor (bFGF, Peprotech). Cells were passaged by manual dissection every 5-7 days at a ratio of 1:3 and medium was changed every 48 hours. In some experiments, hESCs were grown on matrigel (BD Biosciences) with hESC culture media supplemented with 30% Hs27-conditioned medium and 4 ng/ml bFGF. In other experiments in which Anti-MUC1* was added, conditioned media and bFGF were omitted; we refer to this as "Minimal Media", (abbreviated MM).

FIG. 1 shows the OCT4 immunofluorescence of human stem cell colonies treated with anti-MUC1*. H9 cells were trypsin-dissociated and seeded in 8-well chamber slides pre-coated with matrigel at $4\times10^4$ cells/well. Media was changed and antibodies added every other day at a final concentration of 1 μg/ml for bivalent anti-MUC1* for five weeks. Cells were stained with an OCT4 specific antibody (Santa Cruz, Clones H-134 and C-10) and DAPI.

FIG. 1 shows that after five (5) weeks of growth, human embryonic H9 stem cells grew 100% pluripotently when cultured in minimal media plus anti-MUC1* antibodies. Cells grown identically, except that they were fed minimal media plus bFGF and 30% conditioned media from feeder cells, proliferated less and differentiated more. Compare DAPI staining of nuclei with OCT4 staining that identifies pluripotent cells. Dotted lines mark the border of the undifferentiated portions.

Example 2

Figure 2:
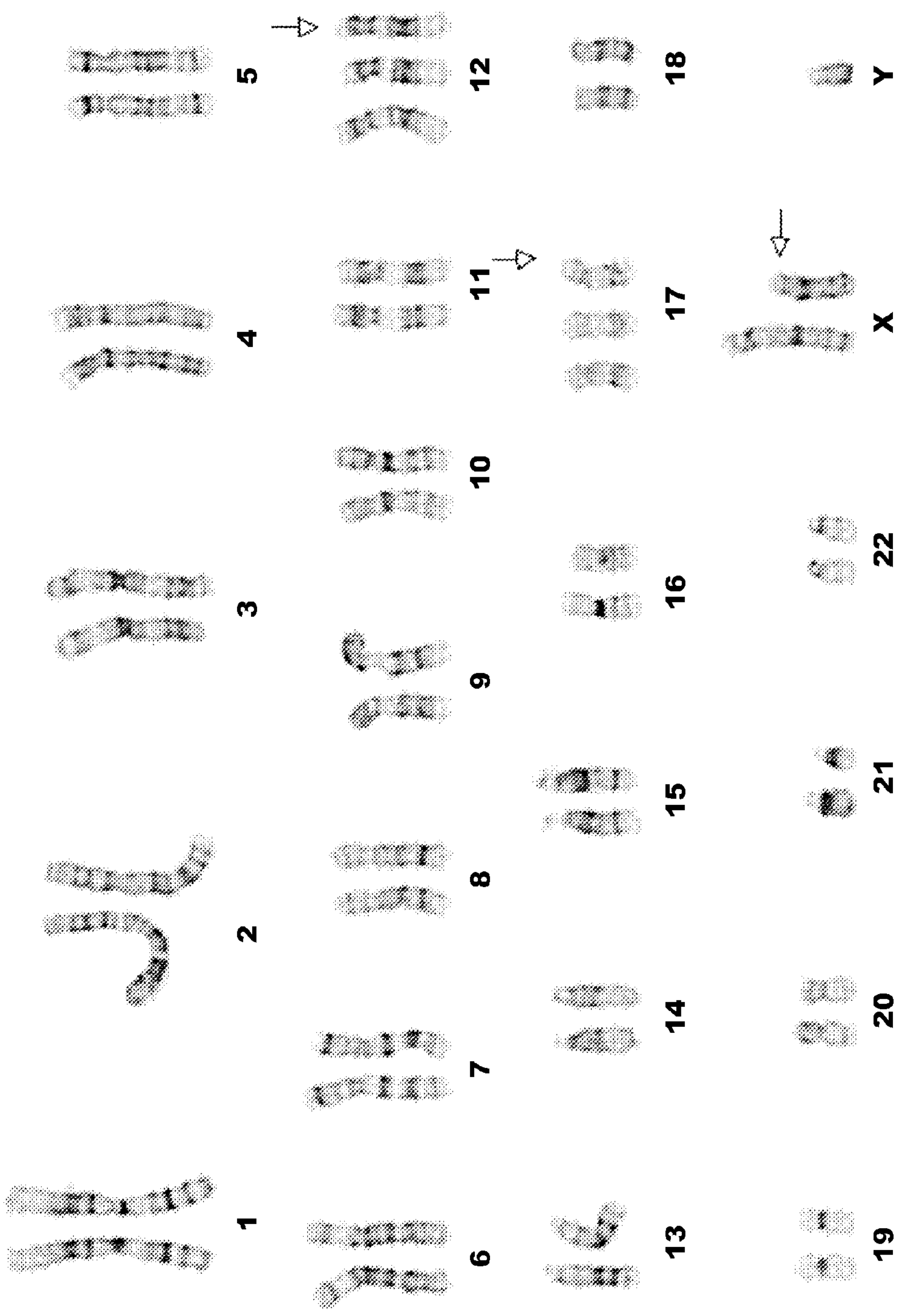
FIG. 2 shows that after 18 passages of human embryonic stem cells on matrigel in anti-MUC1* and minimal media alone, karyotype of BG01v/hOG was unchanged.

Pluripotent Stem Cells Cultured in Anti-MUC1* Over Matrigel Maintain Stable Karyotype and Differentiate Normally BG01v/hOG hu ES cells (Invitrogen) were plated onto Matrigel and cultured in Minimal Media (see Example.1) plus a rabbit polyclonal anti-MUC1* antibody (SRY 2a), at 80 ng/ml for 18 passages over the course of six (6) months. Cells were pelleted, DNA extracted and outsourced for karyotyping. FIG. 2 shows that the karyotype at the end of 18 passages was unchanged. Note that this stem cell line has tri-somal abnormalities; however it is pertinent that the karyotype was stable and unchanged by culturing in anti-MUC1* in the absence of other growth factors.

Figure 3:
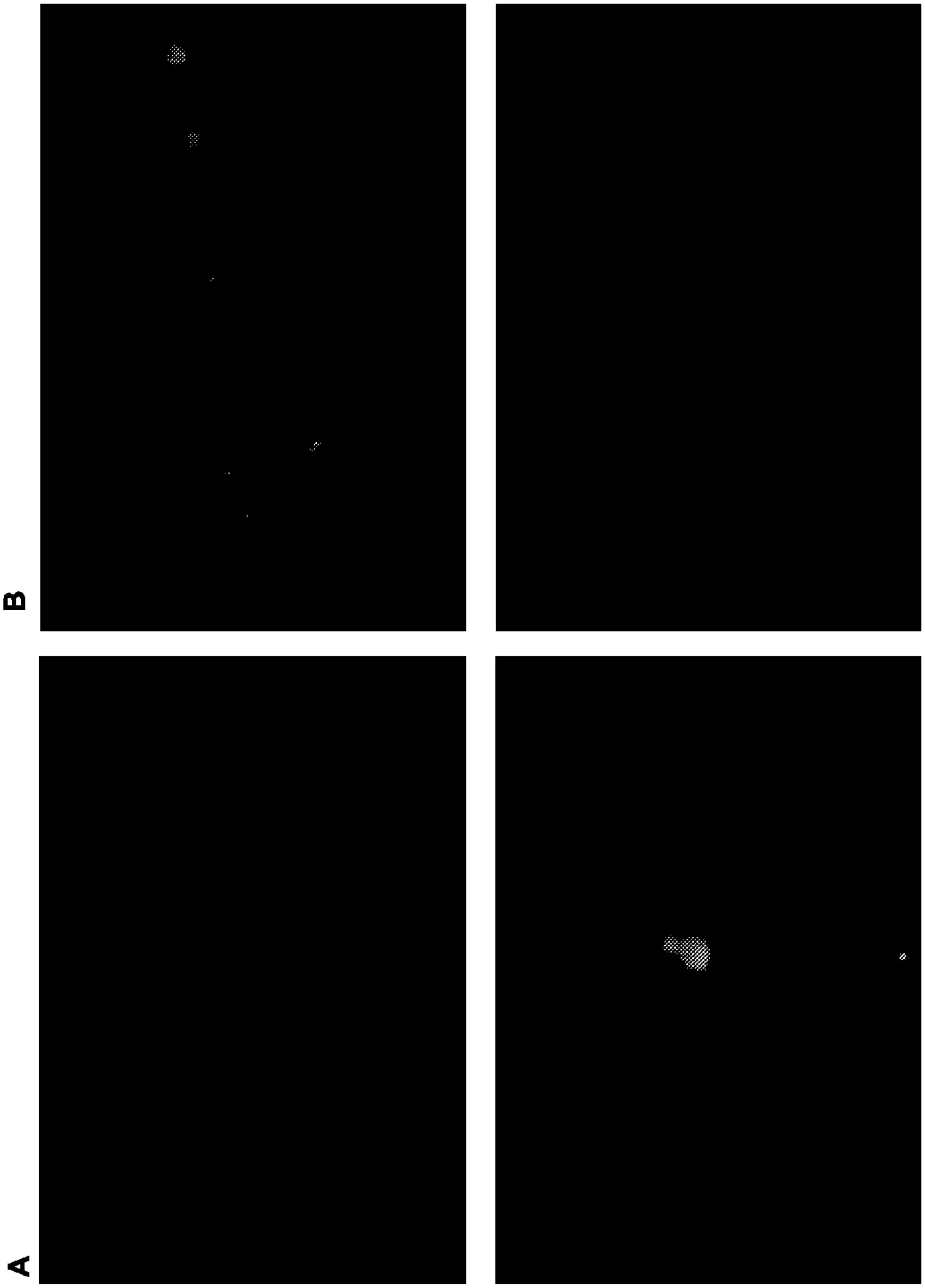
FIGS. 3A-3D show that human embryonic stem cells cultured on matrigel in anti-MUC1* and minimal media alone, were able to differentiate down the 3 germlines: A) OCT4– negative indicates that the cells have differentiated; B) positive for alpha-fetoprotein indicates differentiation along the endoderm germline; C) positive for Nestin indicating differentiation down the ectoderm germline; and D) positive for smooth muscle actin, indicating differentiation down the mesoderm germline.

From this same batch of multiply passaged BG01v/hOG cells, undifferentiated stem cells were harvested by treatment with collagenase then suspended in minimal media for 14 days. Note that during this period, anti-MUC1* antibody is withdrawn to promote differentiation. This allowed the cells to form embroid bodies, which were plated onto gelatin for 7 days, then stained with antibodies that recognize markers of the three germlines: FIG. 3 A) Cells were OCT4– negative, indicating that they had differentiated; B) alpha fetoprotein-positive, which is a marker for endoderm; C) nestin-positive, a marker for ectoderm; and D) positive for smooth muscle actin, which is a marker for mesoderm germline.

Example 3

Surfaces that Promote Pluripotent Stem Cell Growth

Surfaces that present a ligand that binds to and dimerizes the extracellular domain of MUC1* provide pluripotent stem cells with a method for adhering to the plate surface and also activate the growth factor receptor function of MUC1*. Cell culture flasks, petri dishes or multi-well plates were coated with a rabbit polyclonal antibody raised against a peptide having the sequence of the MUC1* extracellular domain:

(SEQ ID NO: 1)
GTINVHDVETQFNQYKTEAASRYNLTISDVSVSDVPFPFSAQSGA.

Antibodies that bind to the sequence given directly above are referred to here as anti-MUC1* antibodies or anti-PSMGFR antibodies. Tissue culture treated, as well as bare plastic, and polystyrene plates were used.

In one example, anti-MUC1* antibody (Zymed: custom antibody service) was added at 30, 100, or 300 ug/ml to wells of a 96-well cell culture treated plate (Tissue Culture Test Plate 96F TPP #92096) and allowed to adsorb overnight at 4 degrees C. Undifferentiated BG01v/hOG (Invitrogen) stem cells were suspended in Minimal Media. Minimal Media is 400 ml DME/F12/GlutaMAX I (Invitrogen#10565-018; 100 ml Knockout Serum Replacement (KO-SR, Invitrogen#10828-028); and 5 ml 100×MEM Non-essential Amino Acid Solution (Invitrogen#11140-050); and 0.9 ml (0.1 mM) β-mercaptoethanol (55 mM stock, Invitrogen#21985-023). The BG01v/hOG stem cells were plated onto anti-MUC1* antibody coated surfaces at a density of 10,000 cells per well. Cells were allowed to adhere for 24 hrs. Cells were then cultured in Minimal Media alone for 5 days, with media changed every 48 hours.

For comparison, cells in control wells were cultured in media supplemented with 4 ng/ml of bFGF and 30% conditioned media from HS27 fibroblasts. FIG. 4 shows the graph from a Calcein-AM (Molecular Probes) staining, in which fluorescence from live cells is measured as a function of anti-MUC1* antibody density on the surface that those cells were grown. The graph of FIG. 4 shows that cells grown on anti-MUC1* surfaces proliferate in the absence of any other growth factors. Growth is only moderately enhanced by the addition of bFGF and uncharacterized factors secreted from feeder cells. As a negative control, an irrelevant antibody was plated onto surfaces. Stem cells that were plated onto these surfaces did not adhere and were either floating or dead by the end of the 24-hour attachment period.

In parallel, the resultant stem cells were double stained with DAPI (nuclear stain) and anti-OCT4. The 1:1 correlation of OCT4 positivity and DAPI staining confirms that the resulting cells were pluripotent, see FIG. 5.

Example 4

Human Pluripotent Stem Cells Proliferate on Anti-MUC1* Antibody Surfaces with or without MUC1* Stimulators Added into Solution Human embryonic stem cell lines were tested for their ability to grow on anti-MUC1* antibody adsorbed to either tissue culture treated plates, polystyrene plates, or chamber slide plates. Anti-MUC1* at 100 ug/ml was adsorbed onto the plates and allowed to adsorb at 4 degrees C. overnight. Undifferentiated human H9 embryonic stem cells were plated at either 10,000 cells or 40,000 cells per well of a 96-well or at 25,000 cells per well of 8-well plates. In all cases, undifferentiated stem cells attached and proliferated on anti-MUC1* surfaces, cultured in minimal media alone or with anti-MUC1* added into minimal stem cell growth media. The undifferentiated H9 stem cells were then cultured in: A) Minimal Media; B) minimal media plus anti-MUC1* antibody at 80 ng/ml; or C) minimal media plus bFGF at 4 ng/ml and 50% conditioned media from inactivated HS27 fibroblast feeder cells. Experiments were performed in triplicate. Undifferentiated stem cells adhered to anti-MUC1* surfaces. Undifferentiated colonies grew fastest when anti-MUC1* antibody was also added into minimal media. However, undifferentiated stem cell colonies of similar morphology and quality developed a day or two later in wells that were cultured in minimal media alone. The amount of proliferation and quality of undifferen十iated stem cell colonies were comparable whether cells were cultured in minimal media, minimal media plus anti-MUC1* or plus bFGF and conditioned media from fibroblasts. Pluripotent stem cells resulted and could be split between days 5 and 7, which is typical for stem cells grown according to standard feeder cell, bFGF protocols. FIG. 6 shows photos of wells grown when cultured in different media. 6A) minimal media; 6B) minimal media plus anti-MUC1* antibody at 80 ng/ml; or 6C) minimal media plus bFGF at 4 ng/ml and 50% conditioned media from fibroblast feeder cells. Panels marked 1 (e.g. A1, B1, C1) are photos taken after 3 days of growth; A2, B2, and B3 are photos of the same wells taken at day 7.

Example 5

Method for Harvesting Stem Cells

The stem cells grown in Example 4 above were ready for harvesting and splitting at day 7. Since cells were immobilized on an anti-MUC1* surface, we reasoned that they could be released by adding a peptide that would compete with the cell surface receptor for binding to the anti-MUC1* antibody on the plate surface. The peptide having the sequence GTINVHDVETQFNQYKTEAASRYNLTISDVSVSDVPFPFSAQSGA (SEQ ID NO:1), corresponds to the extracellular domain of the MUC1* receptor and was also the peptide that the anti-MUC1* antibody was raised against, is referred to here as the MUC1$^*_{ecd}$ peptide or PSMGFR peptide. The MUC1$^*_{ecd}$ peptide was added to the growing stem cells at a concentration of 10 uM and incubated for 30 minutes. At that time, it was observed that the stem cells had been released from the surface. Stem cells were collected in the supernatant, rinsed and re-plated onto fresh anti-MUC1* surfaces, where cells adhered and continued to proliferate. This procedure was also successfully performed using human embryonic stem (huES) cell line BG01v/hOG (Invitrogen), then huES H9s. FIG. 6D shows H9 stem cells that were grown on anti-MUC1* antibody surfaces, cultured from single cells, then harvested by competitive peptide release, and re-plated onto fresh anti-MUC1* surfaces where they continued to proliferate.

Example 6

Figure 7:
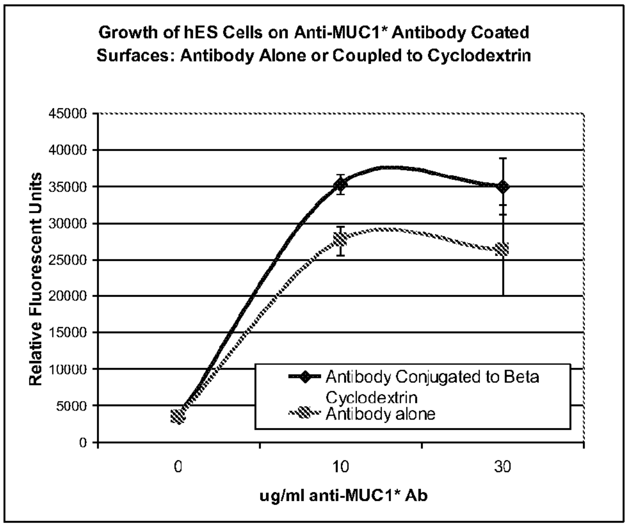
FIG. 7 is a graph of stem cell growth on surfaces coated with anti-MUC1* antibody or the same antibody coupled to beta-cyclodextrin. It shows enhanced cell adhesion and growth when antibody is coupled to the dextrin.

Anti-MUC1* Antibody Coupled to Beta-Cyclodextrin Stimulates Solution Interaction of MUC1* Growth Factor with Cell Surface Receptors Anti-MUC1* antibodies were covalently coupled to carboxy-β-cyclodextrin (Cβ-CD) according to a standard coupling protocol (Fraschini, C.; Vignon, M. R. Selective oxidation of primary alcohol groups of β-cyclodextrin mediated by 2,2,6,6-tetramethylpiperidine-1-oxyl radical (TEMPO). Carbohydrate Research 2000. 328(4):585-589). 96-well cell culture treated plates (Tissue Culture Test Plate 96F TPP #92096) were coated with anti-MUC1* coupled to beta-cyclodextrin, at 0, 10, 30, 100, 300, or 1000 ug/ml final antibody concentration; the concentration of beta-cyclodextrin in each well was kept constant with only the concentration of the antibody varied. As a control, anti-MUC1* antibodies were directly adsorbed onto the plates without cyclodextrin. Single cell suspensions of BG01v/hOG stem cells were made, and cells were plated at a density of 10,000 cells/well in minimal medium. Stem cells attached to, and proliferated on both the antibody surfaces and antibody coupled to cyclodextrin surfaces. No other growth factors were added. Two days post-plating, live cells were assayed by Calcein-AM reagent. The graph of FIG. 7 shows that stem cell growth in minimal media is supported by anti-MUC1* antibodies presented on beta cyclodextrin and that the amount of antibody required is less than naked antibody adsorbed onto the growth plate, perhaps because of the 3-dimensional presentation of the antibody to the growing cells.

Example 7

Figure 8:
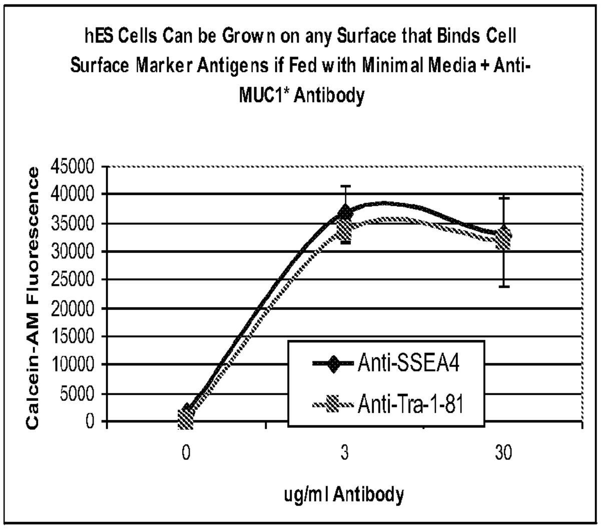
FIG. 8 shows that hu ES cells can be cultured by attaching them to surfaces coated with antibodies that bind to stem cell surface marker proteins SSEA4 and Tra 1-81 if cultured in minimal media plus 80 ng/ml of anti-MUC1* antibody.
Figure 9:
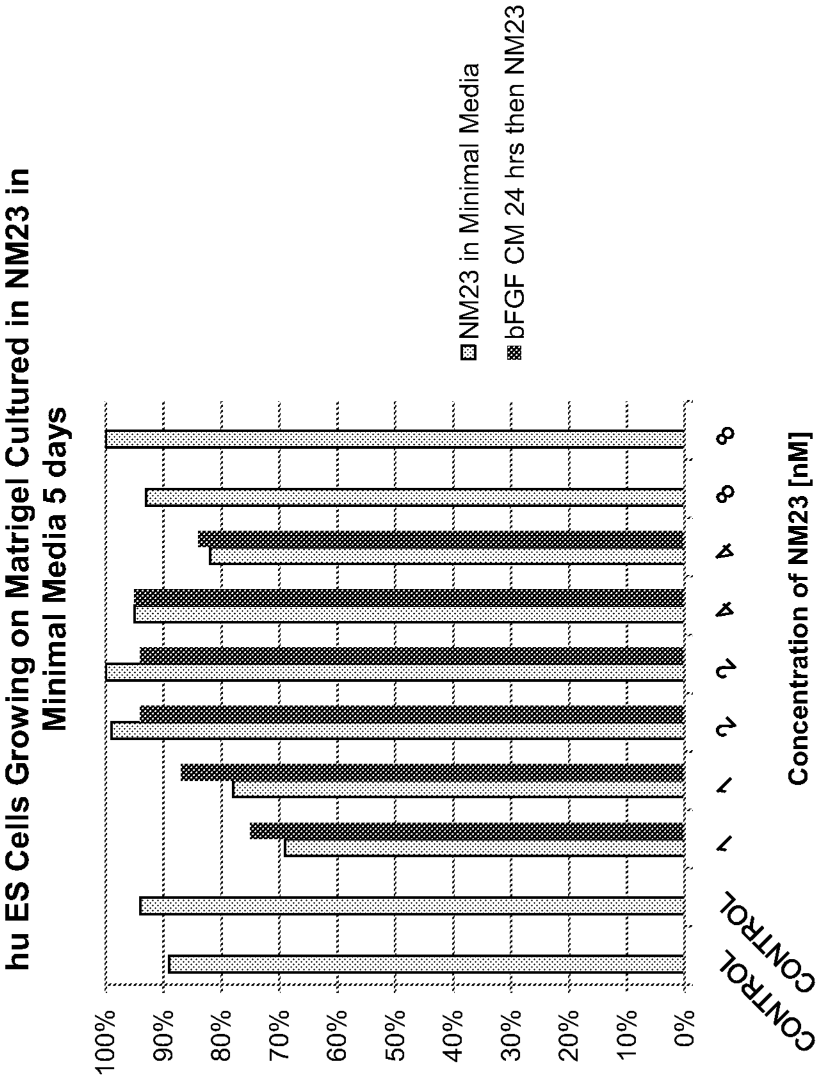
FIG. 9 shows that hu ES cells on matrigel grow at least as well as the state of the art when they are cultured in minimal media plus NM23. The graph compares the growth of hu ES H9 cells on Matrigel when they are cultured in the standard 4 ng/ml bFGF plus HS27 conditioned media from fibroblasts (Control) and growth in minimal stem cell media plus NM23 at the concentrations indicated. Percent undifferentiated growth was calculated by a blinded count of both undifferentiated and differentiated colonies, then calculated as percent. Only cells that were totally undifferentiated were scored undifferentiated.

Antibodies Against any Cell Surface Antigen Will Allow Stem Cells to Attach to a Surface and will Proliferate if Cultured by Conventional Means or by Adding Anti-MUC1* Antibody to Minimal Media SSEA4, Tra 1-60, and Tra 1-81 antibodies promote pluripotent stem cell growth when cultured in minimal media plus anti-MUC1* antibody. 96-well cell culture treated plates (Tissue Culture Test Plate 96F TPP #92096) plates were separately coated in triplicate at 4° C. with Anti-SSEA4 (Santa Cruz), Anti-Tra 1-60 (Santa Cruz), or Anti-Tra 1-81 (Santa Cruz) antibodies at final concentrations of 0, 3, 10, 30, and 100 ug/ml in sterile PBS. The following day, cells were rinsed with PBS. BG01v/hOG human embryonic stem cells (Invitrogen) that had been grown on matrigel and cultured in minimal stem cell growth media plus 30% conditioned media from fibroblasts plus 4 ng/ml bFGF were used to make single cell suspensions. Cells were plated in each well at a density of 10,000 cells per well in Minimal Media. The following day, medium was removed from wells, and replaced with Minimal Media plus 80 ng/ml Anti-MUC1* antibody. Media was changed every other day, and cells were assayed by Calcein-AM reagent. FIG. 8 shows that stem cells can attach to a surface via interaction with a cell surface protein and its cognate antibody, then can be cultured in minimal media plus anti-MUC1* antibody or with any standard stem cell growth media.

Similarly, H9 undifferentiated stem cells were plated at a density of 10,000 cells per well of a 96-well plate onto which anti-SSEA4 antibodies had previously been adsorbed (100 ug/ml). The stem cells were cultured for eight (8) days in minimal stem cell growth media plus anti-MUC1* antibody at 80 ng/ml. Undifferentiated stem cell colonies developed and proliferated.

Experiments were performed in parallel that showed that H9 human embryonic stem cells bound to anti-SSEA4 and anti-Tra 1-81 that had been adsorbed onto the surface of 96-well and 12-well plates. Cells were then cultured in either standard stem cell growth media containing bFGF at 4 ng/ml and 50% conditioned media from HS27 fibroblast feeder cells, or in minimal media plus anti-MUC1* antibodies at 80 ng/ml, or in minimal media plus recombinant NM23-S120G at 8 nM. Undifferentiated stem cell colonies formed in all cases that were morphologically identical stem cell colonies grown by standard methods. When either an irrelevant antibody replaced anti-MUC1* antibodies, or cells were cultured in minimal media alone, stem cells died within about a day.

Example 8

Addition of MUC1*$_{ecd}$ Peptide Induces Differentiation

Undifferentiated human stem cells growing on either feeder cells, matrigel or growth surfaces can be rapidly induced to differentiate by the addition of the MUC1*$_{ecd}$ peptide. The peptide competes with the natural ligand for binding to the MUC1* growth factor receptor; the interaction of the natural ligand with MUC1* promotes pluripotent cell growth. Blocking this interaction inhibits the pluripotent stem cell growth and induces cells to differentiate. H9 stem cells growing on matrigel differentiated about three times faster after treatment with the MUC1*$_{ecd}$ peptide. The MUC1* extra cellular domain peptide can be used to harvest stem cells from surfaces coated with ligands of MUC1*. Increased rates of differentiation were prevented by incubating the harvested cells with either anti-MUC1* to compete away the peptide, followed by rinsing and re-plating.

Example 9

NM23 in Minimal Media is Equivalent to State of the Art bFGF Plus Conditioned Media from HS27 Fibroblast Feeder Cells for the Culture of Human Stem Cells Undifferentiated H9 human embryonic stem cells were harvested by manual dissection. Colony pieces, approximately 0.1 cm on edge, were mixed into minimal media and uniformly distributed onto 24-well plates that had been coated with stem cell quality matrigel according to the manufacturer's directions. Undifferentiated colonies pieces from (3) wells of a 6-well plate were transferred to a 24-well plate. Recombinant NM23-S120G (mutant that preferentially forms dimers) at either 4 nM or 8 nM concentration in minimal media (MM) was compared to the state of the art, which is currently 4 ng/ml bFGF (basic fibroblast growth factor) plus 50% conditioned media (CM) from inactivated HS27 fibroblast feeder cells. We also tested the effect of treating the freshly plated cells with bFGF/CM for the first 24 hours then switching to the NM23 in MM. After 4 days in culture, the numbers of undifferentiated versus differentiated colonies were counted. The results are graphed in FIG. 9. The bars marked CONTROL refer to the standard method of culturing over matrigel in 4 ng/ml bFGF and 50% CM from inactivated HS27 fibroblast feeder cells. The graph shows that: 1) cells growing in NM23+MM grew faster than bFGF+CM; 2) NM23+MM had less differentiation than the state of the art; 3) adding bFGF+CM for the first 24 hours was slightly worse than directly culturing in NM23+MM; and 4) the trend appears to indicate that the highest concentration of NM23 (8 nM) was best.

Cells were split on day 5 and re-plated over matrigel. For the next 5 days, cells were cultured in either 4, 8, 16, 32 or 64 nM. Results showed that increased concentrations of NM23-S120G worked better. 16 nM and 32 nM NM23-S120G produced roughly the same number and quality of undifferentiated colonies as the bFGF+CM control. At 16 nM, each well yielded 4-5 colonies where only 1 was differentiated; 32 nM wells each yielded 3 colonies total with 1 partially differentiated; bFGF+CM controls produced 2 undifferentiated colonies and 1 partially differentiated in one well and 1 undifferentiated, 2 fully differentiated in the other well. NM23-S120G produced much larger colonies than bFGF/CM.

Example 10

Anti-MUC1* Coupled to Cyclodextran Plus Anti-MUC1*or bFGF-Anti-MUC1* Antibodies Coupled to Cyclodextran Promote Stem Cell Attachment and Growth in Either Traditional Media or Minimal Media Plus MUC1* Stimulators Human embryonic H9 stem cells that had been growing by standard methods on HS27 fibroblasts, then on matrigel for 2 passages were manually dissected and harvested as described in Example 9. Undifferentiated colony pieces from 2 wells of a 6-well plate were passaged onto wells of a 24-well plate that were coated with anti-MUC1* antibody covalently coupled to cyclodextran. Cells were then cultured in either anti-MUC1* antibody in Minimal Media at a final concentration of 160 ng/ml or 4 ng/ml bFGF and 50% HS27 conditioned media (CM). Cells attached within hours grew as one would expect for growth over feeder cells or matrigel, except with an accelerated growth rate. Cells were ready to be split at between day 5 and 6 post plating. Undifferentiated colony pieces were manually harvested and re-plated onto new cyclodextran-anti-MUC1* coated plates where they continued to proliferate and form undifferentiated colonies. Cell number, colony morphology and inhibition of differentiation were comparable between wells cultured in anti-MUC1* and bFGF plus HS27 CM.

Example 11

Method for Coupling Ligands to Cyclodextran

Dextran Carboxylation: Materials: Dextran 500 (Avg. MW is 500 kD, Aldrich cat. #31392, isolated from *Leuconostoc* spp., Sigma-Aldrich, St. Louis, Mo.); Bromoacetic Acid and NaOH (Sigma-Aldrich); Type I $H_2O$ (Ricca Chemical Company, Arlington, Tex.); 20,000 MWCO dialysis tubing, or slides (Fisher Scientific, Waltham, Mass.).

Procedure: A 2N solution of NaOH was prepared with Type I $H_2O$. Into a clean, dry 20 mL scintillation vial was added 6 mL of the above solution. To this was added 834 mg of bromoacetic acid, solution became cloudy after dissolution. Then 1.00 g of Dextran 500 was added to the vial and the solution was subjected to vortexing and light ultrasonication to give complete dissolution within 5 minutes. This solution was then stirred at room temperature for 24 hours. Solution was then dialyzed against running tap water for 8 h, then dialyzed against 0.1 N HCl for 18 h, then dialyzed against distilled water for 12 hours. Solution then freeze-dried and stored under argon at −20° C.

Dextran-Protein/Antibody Coupling:

Materials: Carboxylated Dextran 500, prepared in-house; 1-Ethyl-3-(3-dimethylaminopropyl)carbodiimide (EDC) (Sigma-Aldrich); N-Hydroxysuccinimide (NHS) (Sigma-Aldrich); Protein or antibody to be coupled; Type I $H_2O$ (Ricca Chemical Company); Ethanolamine (Sigma-Aldrich).

Procedure: A solution of 0.5 mg/mL carboxylated dextran 500 in Type I $H_2O$ was prepared. A solution of 100 mM EDC/100 mM NHS in Type I $H_2O$ was prepared. In a 1.5 mL eppendorf tube, an aliquot 1 mL of the dextran solution was added to 12 μL of the EDC/NHS solution. The mixture was vortexed, and allowed to rock at room temperature for 15 minutes to activate the carboxylic acid residues. Meanwhile, 6.67 nmol of protein or antibody (dissolved in an appropriate buffer) was aliquoted into a separate tube. After the 15 minute activation, 110 μL of the activated dextran solution was pipeted into the tube containing the protein or antibody to be coupled. The solution was gently vortexed to mix, then lightly rocked tube at room temperature for 2 h. 5 μL of ethanolamine was added into the tube and allowed to rock for an additional 15 minutes at room temperature. The contents of the tube were dialyzed against phosphate buffered saline (pH 7.4) at 4° C. for at least 18 hours. The solution may be used fresh or can be lyophilized, stored at −20° C., and subsequently reconstituted prior to use.

Note that we empirically determined the optimal amounts of carboxylation and concentrations of protein to be coupled by testing the growth of stem cells on 24 surfaces in which carboxylation and protein concentration were systematically varied.

Example 12

Figure 10:
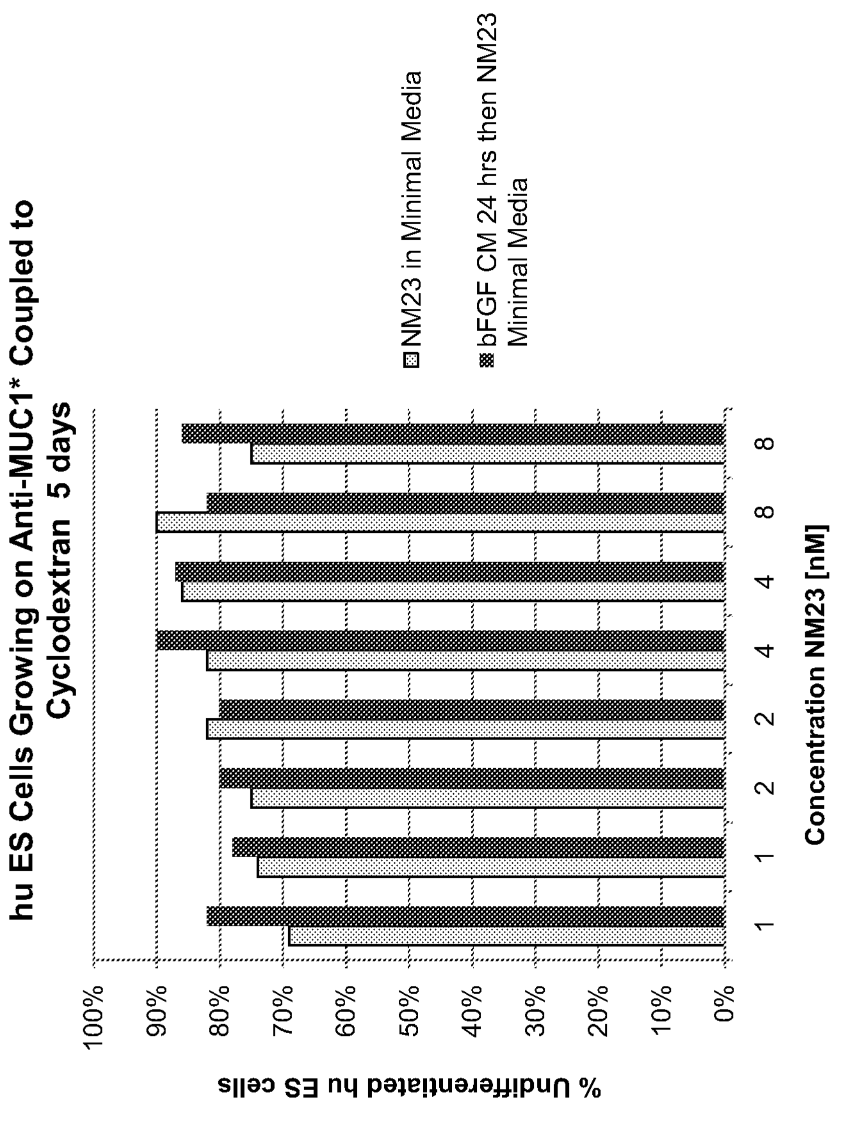
FIG. 10 shows hu ES cells growing on surfaces coated with anti-MUC1* covalently coupled to cyclodextran and cultured until ready to split in minimal media plus NM23 at indicated concentrations. One set of cells was first cultured in 4 ng/ml bFGF plus 50% HS27 fibroblast conditioned media (CM) for the first 24 hours. The graph shows that bFGF and CM do not benefit cell growth or differentiation state if adequate amounts of NM23 are added.
Figure 11A:
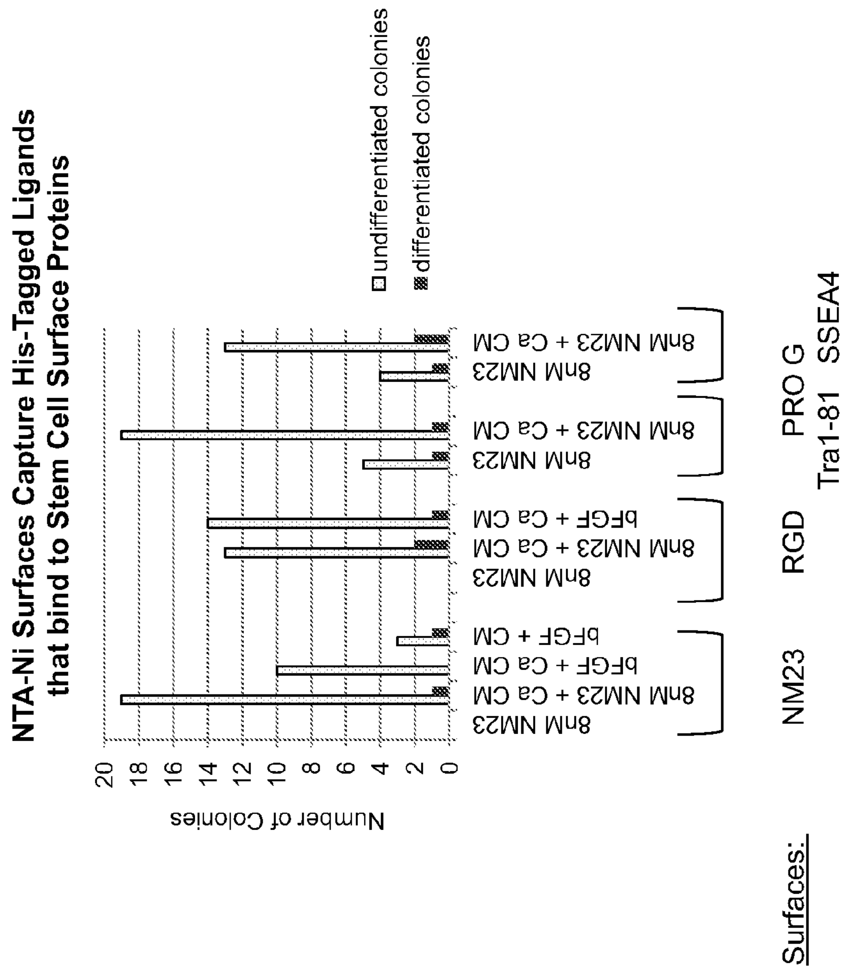

H9 Stem Cells Attached to Anti-MUC1* Coupled to Cyclodextran and Cultured in Either NM23-S120G in Minimal Media or bFGF in HS27 Conditioned Media 24 well plates were coated with anti-MUC1* coupled to cyclodextran, as described in Example 11. H9 cells were passaged onto these surfaces as described in Example 9 and cultured in recombinant NM23-S120G in minimal media at a final concentration of 1 nM, 2 nM, 4 nM, or 8 nM. In another condition, cells were treated with 4 ng/ml bFGF and 50% HS27 conditioned media (CM) for 24 hours before being switched to Nm23-S120G in minimal media. Experiments were performed in duplicate. After 4 days growth, the number of undifferentiated versus differentiated colonies were counted and graphed as percentage undifferentiated colonies to the total number of colonies. Only colonies that were 100% undifferentiated were counted as undifferentiated. FIG. 10 shows that bFGF plus CM is only helpful when the concentration of NM23-S120G is insufficient. Further, results showed that NM23-S120G in minimal media performed as well or better than bFGF plus fibroblast feeder cell conditioned media, in terms of colony morphology, number and inhibition of differentiation.

Example 13

Procedure for Coating Culture Flasks with NTA-Ni

Materials: 24-well carboxylic-acid-presenting-surface cell-culture plate (BD Biosciences Purecoat: #356775); 1-Ethyl-3-(3-dimethylaminopropyl) carbodiimide (EDC); N-Hydroxysuccinimide (NHS); $N_\alpha$,$N_\alpha$-Bis(carboxymethyl)-L-lysine Hydrate; Type I $H_2O$; Sterile syringe (20 mL); 0.45 μm PVDF-membrane syringe filters.

Procedure: 75 mL of 10 mM EDC/10 mM NHS solution per plate to be derivatized was prepared. Using a sterile syringe and syringe filter, the EDC/NHS solution was filtered into each well, filling the wells ~80%. Plates were covered and shaken gently on a plate-shaker at room temperature for 15 minutes. While the plates were shaking, ~40 mL of 10 mM $N_\alpha$,$N_\alpha$-bis(carboxymethyl)-L-lysine hydrate per plate were prepared. After the 15 minutes activation of the plates, the plates were emptied and rinsed 3× with Type I water. Using a fresh sterile syringe and syringe filter, the solution of $N_\alpha$,$N_\alpha$-bis(carboxymethyl)-L-lysine hydrate were filtered into each well, filling the wells about halfway. The plates were covered and shaken gently at room temperature for 3 hours. After 3 hours, the plates were emptied and rinsed 5× with Type I water. Remaining activated NHS-esters were quenched at this point by adding a sterile solution of 1% ethanolamine and incubating at room temperature for 15 minutes, then adding a sterile solution of 10% sodium carbonate and incubating at room temperature for 30 minutes. This can also be accomplished by storing the plates in sterile, Type I $H_2O$ for at least 48-72 hours at 4° C. Once residual NHS esters have been either quenched or hydrolyzed back to the carboxylic acids, wells must be filled with sterile, Type I $H_2O$, then wrapped in parafilm, covered, wrapped in tin foil, and stored at 4° C. Plates should be rinsed again with sterile, Type 1 $H_2O$ immediately prior to use. A 1% nickel sulfate solution was added to the plates, then rinsed with PBS prior to use.

Note that the use of the ethanolamine solution will convert the residual NHS esters into amides presenting a hydroxyl head group. This will alter the surface chemistry. If this is not desirable, use of either the carbonate-solution soak or long-term-aqueous soak will hydrolyze all remaining NHS esters back to the original carboxylic acids.

Example 14

H9 Stem Cells Attached to NTA-Ni Plates that were Coated with Ligands Bearing Histidine Tags 12-well plates were derivatized with NTA-Ni as described in Example 13. Histidine tagged NM23-S120G, a synthetic peptide of sequence HHHHHHSSSSGSSSSGSSSSG-GRGDSGRGDS (SEQ ID NO:5) (RGD peptide), and recombinant, histidine tagged Protein G (Minerva) were separately added to NTA-Ni coated wells at a final concentration of 200 nM and incubated for 15 minutes. Plates were rinsed in PBS. To the Protein G wells, anti-SSEA4 and anti-Tra 1-81 were added at 200 nM and incubated for 15 minutes, then washed with PBS. Colony pieces were harvested as described in Example 9 from 3 wells of a 6-well plate of H9 cells growing over matrigel for 2 passages were plated onto the wells. The stem cells were cultured in either 8 nM NM23-S120G in minimal media, 4 ng/ml bFGF plus HS27 CM, 8 nM NM23-S120G plus 50% conditioned media collected from T47D MUC1*-positive cancer cells ("Ca CM"), or 4 ng/ml bFGF plus 50% Ca CM. Cells attached to the plates within 24 hours and undifferentiated stem cell proliferation was observed. On Day 3 post plating, undifferentiated and differentiating colonies were counted and plotted, See FIG. 11A. Representative photos (40×) were taken of: B) NM23-S120G surface and cultured in 8 nM NM23-S120G plus 50% Ca CM; C) RGD peptide surface and cultured in 8 nM NM23-S120G plus 50% Ca CM; D) RGD peptide surface and cultured in 4 ng/ml bFGF plus 50% HS27 CM; E) Protein G surface, anti-SSEA4 then cultured in 8 nM NM23-S120G plus 50% Ca CM; F) Protein G surface, anti-Tra 1-81 then cultured in 8 nM NM23-S120G plus 50% Ca CM; G) RGD peptide surface and cultured in 4 ng/ml bFGF plus 50% Ca CM. The best conditions for this experiment were obtained from His-tagged Protein G attached to the NTA-Ni surface, then affinity attached to anti-SSEA4 or Tra 1-81, then cultured in NM23-S120G in MM or CaCM.

In similar experiments, conditioned media from other MUC1*-positive cancer cells (ZR-75-1 and ZR-75-30) was used and produced the same results.

Example 15

Figure 12:
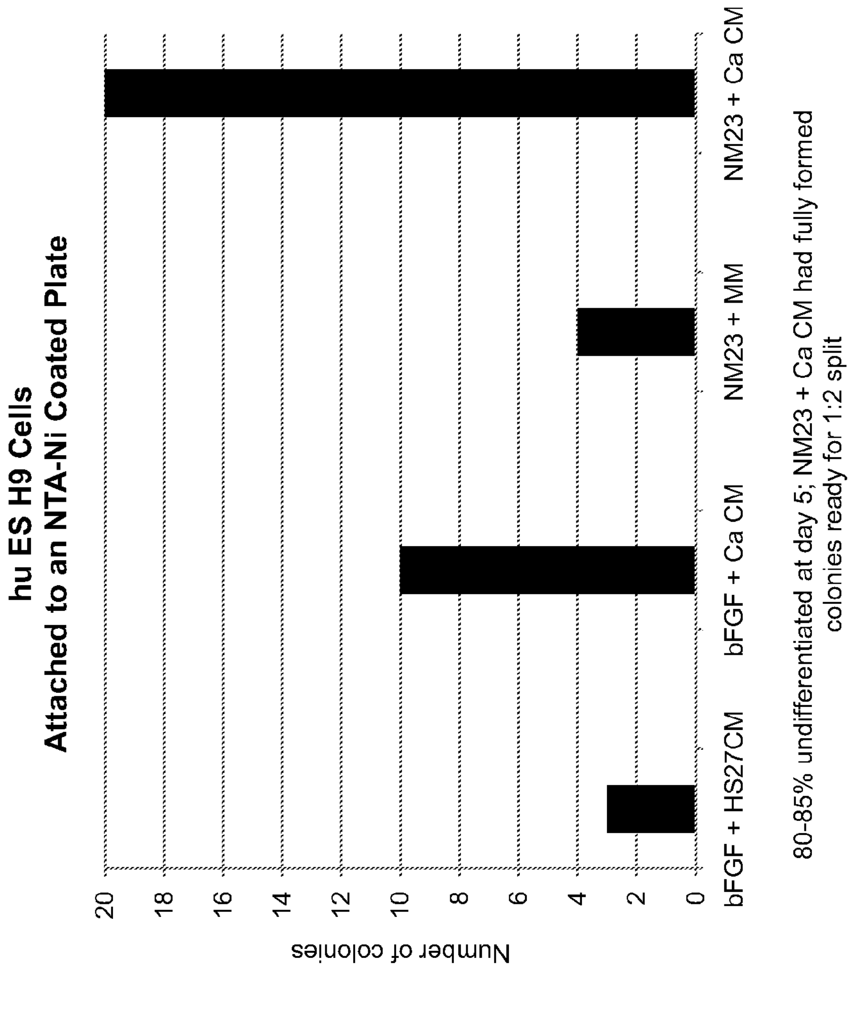
FIG. 12 shows that conditioned media from MUC1*-positive cancer cells (Ca CM) promotes the growth of and inhibits differentiation of hu ES cells to a far greater extent than the standard fibroblast conditioned media (CM). Further, NM23 worked much better than the standard bFGF when added to Ca CM.

Conditioned Media Collected from MUC1*-Positive Cancer Cells Promotes Stem Cell Growth and Inhibits Differentiation Better than Conditioned Media from Fibroblasts Human embryonic stem cells (H9s) were grown according to standard methods on matrigel in 6-well plates then harvested by manual dissection. Colony pieces from (3) wells of the 6-well plate were distributed over the wells of a 24-well NTA-Ni coated plate. We were curious to see if proteins on the cell surface or proteins in the media would adhere to the metal chelate attached to the plate surface. The media that was added to the plated colony pieces was either: a) 4 ng/ml bFGF plus HS27 (fibroblast) conditioned media (CM); b) 4 ng/ml bFGF plus conditioned media from T47Ds (a MUC1* positive breast cancer cell line, CM from these cells referred to here as "Ca CM"); c) 4 nM NM23 in minimal media ("MM"); d) 8 nM NM23 in MM; e) 4 nM NM23 in Ca CM; or f) 8 nM NM23 in Ca CM. After 24 hours, it was observed that cells in either minimal or CM or Ca CM had attached to the surface, even though there was no obvious reason why cells in bFGF/CM or bFGF Ca CM should attach; recall that NM23 that we used was a histidine-tagged recombinant protein that would be readily captured by the NTA-Ni plate. It was observed that cells growing in the cancer cell conditioned media, Ca CM, were growing much better than the other conditions. After 6 in days in culture, with media change every 48 hours, the plates were analyzed for stem cell colony morphology, numbers of colonies and degree of differentiation. Stem cells cultured in 4 ng/ml bFGF plus cancer cell conditioned media formed many more colonies and had much less differentiation (none) than the control of bFGF plus HS27. Cells cultured in NM23 alone grew and formed colonies, but cells cultured in NM23 plus cancer cell conditioned media formed more colonies than any other condition and the colonies were about 80-85% undifferentiated and fully formed and ready to be split, whereas state of the art methods on feeder cells or matrigel would take 9 days to reach the same stage, albeit with 30-40% differentiation on average. FIG. 12 shows a graph of colony number at day 9; NM23 plus cancer cell conditioned media (Ca CM) we have graphed at 20 colonies but the cells had completely covered the entire well and could not actually be counted. At day 9, there were still undifferentiated portions roughly equal to the percentage of the control bFGF plus HS27 fibroblast conditioned media (HS27CM), although in the NM23 stimulated wells, cells proliferated much faster.

Example 16

Antibodies that Bind to Peptide Regions that are Distal to the Cell Surface are Preferred for Cellular Adhesion Antibodies that bind to portions of the MUC1* extra cellular domain that are distal to the cell surface are better for facilitating stem cell adhesion than antibodies that bind to regions close to the cell surface. The extra cellular domain of MUC1* is about 45 amino acids in length. Polyclonal antibodies that were raised against the 45 amino acid peptide, referred to here and in previous applications as PSMGFR having the sequence GTINVHDVETQFNQYKTEAAS-RYNLTISDVSVSDVPFPFSAQSGA (SEQ ID NO:1) facilitated stem cell adhesion to surfaces to which they were attached. A screen of monoclonal antibodies showed that those that recognized portions of MUC1* extra cellular domain close to the cell surface did not promote stem cell adhesion to surfaces even though those same monoclonals stimulated stem cell growth when added into the media. To identify hybridomas that produced antibodies that bound to distal portions of the MUC1* receptor, we adsorbed hybridoma supernatants onto the wells of a 96-well plate, then plated undifferentiated colony pieces harvested from BG01v/hOG cells growing on Matrigel. Supernatants from three (3) clones enabled stem cell adhesion. Minimal Media was changed every 48 hours and proliferating undifferentiated stem cell colonies were photographed on day 9 post plating, see FIG. 13.

In a follow up experiment, an ELISA assay was performed to determine if the antibodies secreted by these hybridomas did in fact bind to the distal portion of the MUC1* extra cellular domain, see FIG. 14. Two deletion peptides were synthesized: one missing the 10 N-terminal amino acids, N-10 PSMGFR, with a sequence QFNQYKTEAASRYNLTISDVSVSDVPFPFSAQSGA (SEQ ID NO:3); and one missing 10 amino acids at the C-terminal end, C-10 PSMGFR having a sequence GTINVHDVETQFNQYKTEAASRYNLTISDVSVSDV (SEQ ID NO:4). The hybridoma supernatants that caused stem cell adhesion to the wells of the 96-well plate, were those that by ELISA assay were shown to bind to the peptide missing the 10 amino acids proximal to the cell surface, but not to the peptide that was missing the distal 10 amino acids. Stem cells plated on the hybridoma supernatants grew into fully formed colonies that were undifferentiated after days of culture in minimal media alone.

Example 17

MUC1* Antibodies are used to Identify Pluripotent Stem Cells from Differentiating Ones The MUC1* ligand, NM23, co-localizes with MUC1* and OCT4 on undifferentiated hESCs but immuno-reactivity of all three proteins is lost in the portion of the colony that has begun to differentiate. Undifferentiated H9 hESC colonies stained positive for NM23, MUC1* and OCT4. Newly differentiating colonies did not react with antibodies against any of the three proteins. Co-expression of NM23 with OCT4 and MUC1* is best seen in colonies that have begun to differentiate. The dotted line marks the border between undifferentiated and differentiated portions of the colonies. Triple staining experiments were performed using: FIG. 15 G) anti-NM23 (green). H) Anti-MUC1* (red). I). anti-NM23 (green), anti-MUC1* (red) and DAPI (blue). A similar colony was stained with: J) anti-NM23 (green). K) anti-OCT4 (red). L. anti-NM23 (green), anti-OCT4 (red) and DAPI (blue). Scale bar=100 μm. Anti-NM23 was purchased from Santa Cruz, Clone NM301 and BD Biosciences, Clone 56. Anti-MUC1* was custom generated from a Minerva PSMGFR peptide by Zymed.

Pluripotent stem cells can be isolated from mixed pools of undifferentiated and differentiated stem cells by labeling live cells with Anti-MUC1* and an antibody such as VU4H5 that binds to full-length MUC1, then sorting by FACS, magnetic cell separation or similar technologies. MUC1*-positivity denotes pluripotent stem cells. Bivalent anti-MUC1* bound to live cells does not interfere with subsequent growth because it functions as a growth factor, so is ideal for cell separations.

Example 18

MUC1* Antibodies are Used to Isolate MUC1* Early Progenitors Away from Later Stage Progenitors—Hematopoietic Stem Cells CD34-positive hematopoietic stem cells (HSCs) obtained from human cord blood (ALLCELLS) were obtained. The cells contained a mixture of CD34+/CD38−, reported to be true HSCs, but also contained CD34+/CD38+ (the next progenitor stage). Cells were defrosted, pelleted, washed in SFEM (Serum-Free Expansion Medium) from StemSpan, and resuspended with SFEM with no growth factors added. Approximately 4000 cells were plated in wells of a 96 well plate covered with poly-HEMA to prevent adhesion. Rabbit polyclonal Anti-MUC1* antibody, generated by immunizing with the PSMGFR peptide, was added to each of 5 wells to a final concentration of 0, 80, 250, and 2000 ng/ml. Cells were photographed at Day 3, FIG. 16 A. Day 5 post plating, antibody was re-added to cells.

Figure 16:
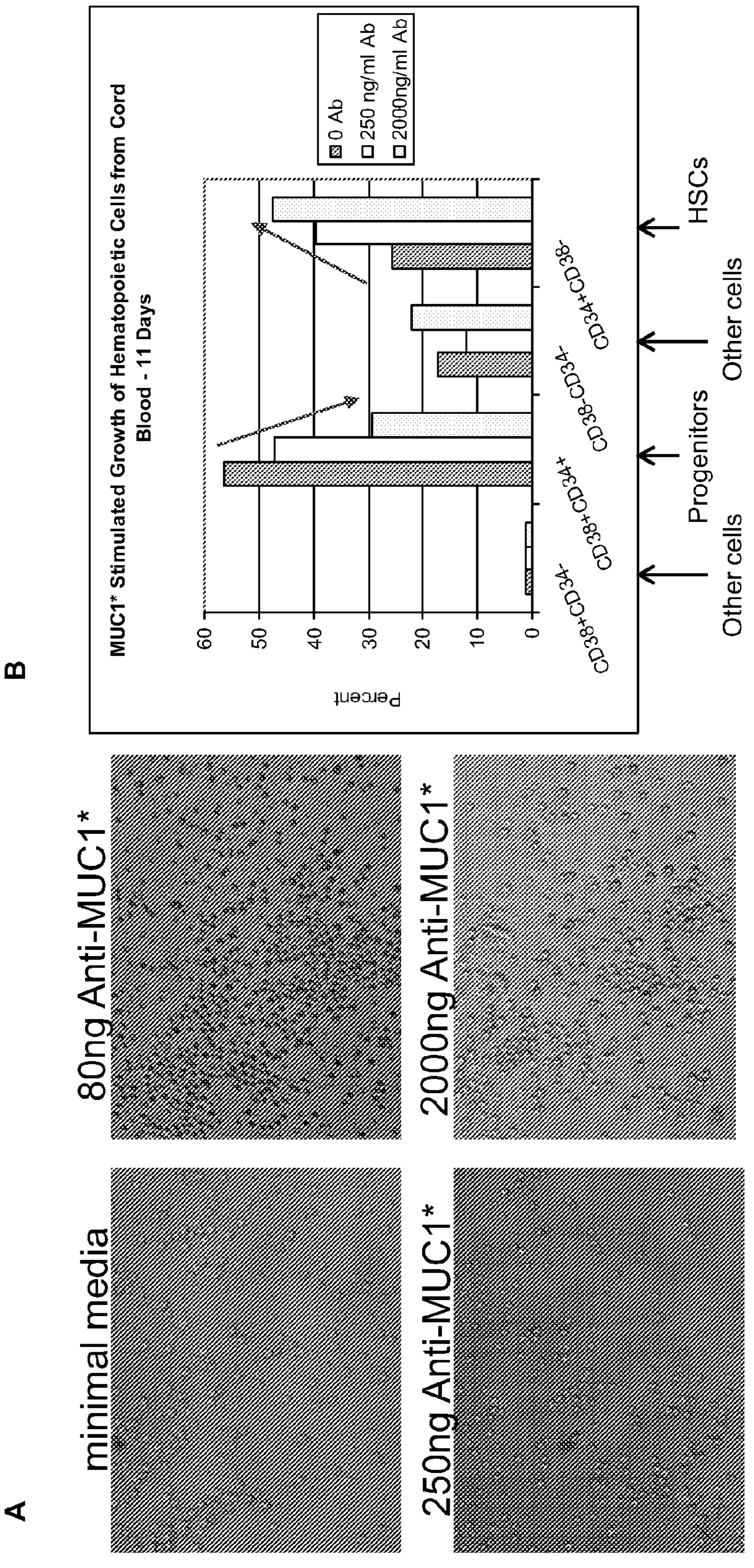
FIGS. 16A-16B show that anti-MUC1* antibody added to stem cell growth media increases the growth of human hematopoietic stem cells (HSCs) (A). (B) FACS analysis shows that the number of cells that remained hematopoietic stem cells, CD34+/CD38−, increased with increasing anti-MUC1* concentration. Conversely, the number of cells that had progressed to the next progenitor stage, CD34+/CD38+ increased as the concentration of anti-MUC1* decreased. These results show that stimulation of MUC1* growth factor receptor inhibited differentiation of HSCs.

11 days post plating, cells were visually inspected and most were still the same diameter as they were when plated, which is an indicator that they were still hematopoietic stem cells and had not progressed to the next progenitor stage. Cells from identical wells were pooled, and stained with anti-CD34-FITC and anti-CD38-PE-Cy5. Cells were analyzed and sorted by FACS (fluorescence activated cell sorting). FIG. 16 B shows that as the concentration of MUC1* antibody is increased, the percentage of cells that remained true hematopoietic stem cells (CD34+/CD38−) increased. The converse was true as well. The percentage of cells that had progressed to the next progenitor stage (CD34+/CD38+) was the highest when the concentration of MUC1* antibody was the lowest. Statistics from representative wells show that stimulation with MUC1* antibody results in more CD34+/38− cells (HSC) and fewer CD34+/38+ (progenitor) cells than unstimulated cells.

Example 19

FACS Sorting of Fetal Liver Cells and Subsequent Growth by MUC1* Stimulation FACS analysis using antibodies that recognized either full-length MUC1 (VU4H5, Santa Cruz Biotechnology; or HMPV, BD Biosciences) or anti-MUC1* (rabbit polyclonal from PSMGFR immunization, Minerva) was performed on a number of different progenitor cells to determine which expressed MUC1*, so that those cells could be isolated and expanded by stimulating the MUC1* receptor. FIG. 17 A shows that neural stem cells (RenCell CX Millipore) express MUC1*. A small number of cells express both cleaved and uncleaved MUC1. Their growth is stimulated by culturing with anti-MUC1* or other agents like NM23 that dimerize MUC1*. Fetal liver cells (ALLCELLS) almost exclusively express MUC1*, FIG. 17 B.

Fetal liver cells were cultured in Minimal Media plus anti-MUC1* antibody at the concentrations indicated in FIG. 18. The growth curve shown shows that the growth of these MUC1* progenitors is stimulated by dimerization of the MUC1* growth factor receptor. At optimal antibody concentration, one antibody dimerizes two MUC1* receptors and when the antibody goes to excess, there is one antibody per receptor and the growth is inhibited. These results show that hematopoietic stem cells as well as other progenitor cells that express MUC1* can be expanded adding agents that dimerize the MUC1* receptor.

Example 20

Figure 19:
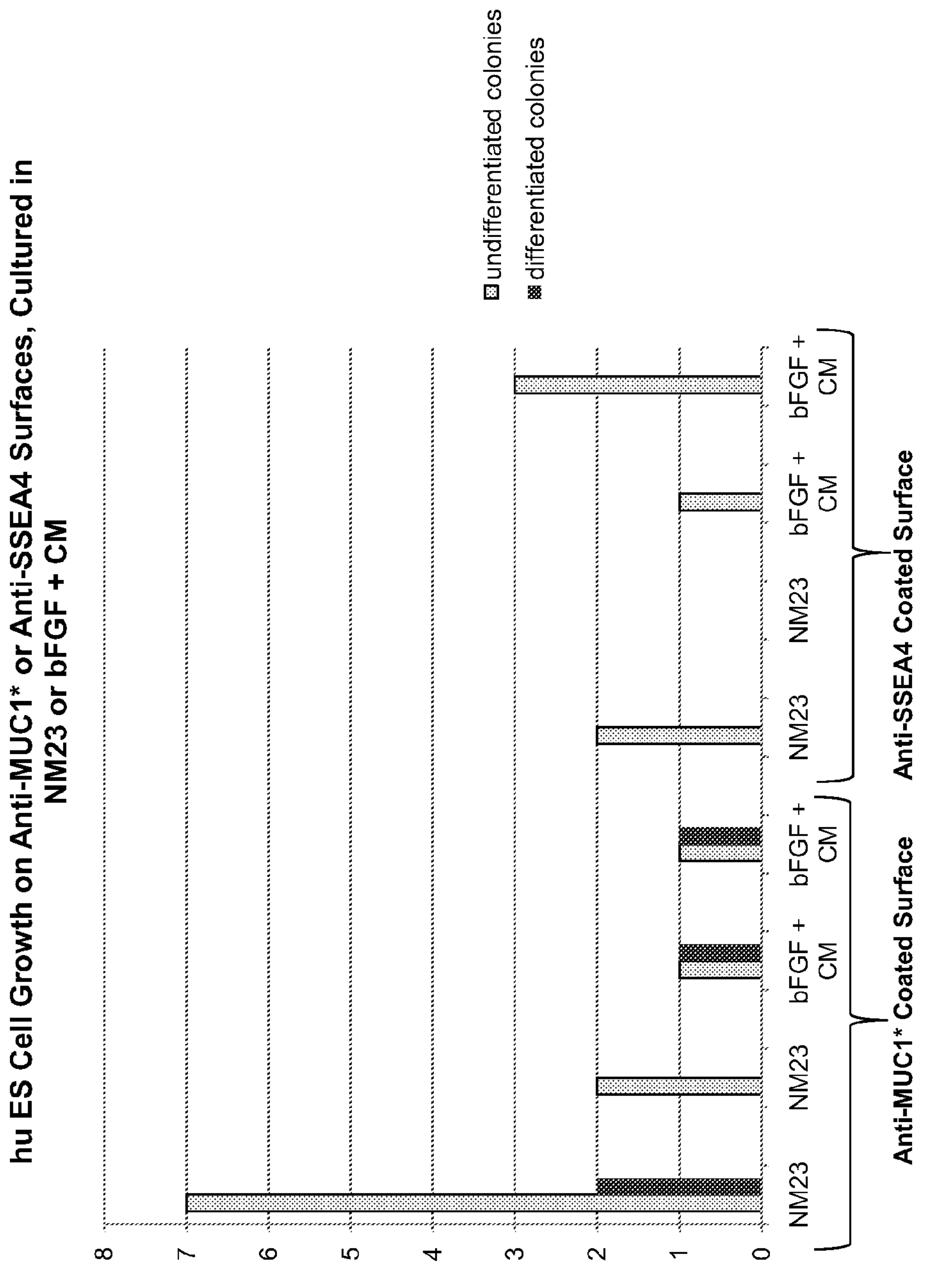
FIG. 19 is a plot of stem cell colonies after hu ES H9 cells were plated on either anti-MUC1* or anti-SSEA4 antibodies that were coated onto 12-well plates, then cultured in either 8nM NM23 or 4 ng/ml bFGF plus 50% HS27 fibroblast conditioned media.

Hu ES Cells Adhere to Surfaces Coated with Antibody Against any Cell Surface Marker Protein and Can be Cultured in Either Standard Stem Cell Media or in Media Containing MUC1* Stimulators 12-well plates were coated with 0.5 ml of either anti-MUC1* or anti-SSEA4 antibody at a concentration of 100 ug/ml. Plates were incubated overnight at 4 degrees C., then rinsed in sterile PBS. Undifferentiated colony pieces from hu ES H9 cells growing on Matrigel were manually dissected, resuspended, then plated over the surfaces. Media was added that contained either a recombinant NM23-S120G (Minerva) at 8 nM final concentration or 4 ng/ml bFGF plus 50% HS27 fibroblast conditioned media. Undifferentiated colonies were manually harvested on day 5 post plating, split and re-plated onto identically coated surfaces. The graph of FIG. 19 shows that stem cells grow on either antibody surfaces if cultured in NM23 in Minimal media (MM) or bFGF plus HS27 conditioned media. It was noted that cells in NM23 treated wells grew considerably faster than in the bFGF treated wells.

Example 21

Identification of Agents in Cancer Cell Conditioned Media that Promote Stem Cell Growth and Inhibit Differentiation Conditioned media from MUC1*-positive cancer cells promotes the growth of human stem cells while inhibiting their differentiation. It would be desirable to identify discrete agents in the cancer conditioned media that affect the growth of stem cells for two reasons. First, these agents could be made synthetically or recombinantly and added as discrete agents to growth media or surface coatings to promote the growth of stem cells and certain early progenitors. Secondly, identification of those agents would enable strategies to suppress them for the treatment of cancers.

To identify proteins in the cancer cell conditioned media Ca CM, one would collect the Ca CM from MUC1*-positive cancer cells and separate out its individual components by, for example, separation on a column, such as ion exchange, size exclusion and the like. The various fractions would be separately, or in combinations, tested for their ability to stimulate undifferentiated stem cell growth. The fraction(s) that imparted the effect would then be analyzed by micro sequencing or mass spec to determine the identity of the components.

A more directed approach is to compare the Ca CM from untreated MUC1*-positive cancer cells to that collected from cells treated with miR-145. miR-145 is a regulatory micro RNA whose expression is upregulated when stem cells transition from undifferentiated to differentiated. Recall that during this transition, MUC1 cleavage ceases and MUC1 expression is down regulated. It has recently been shown that miR-145 silences MUC1. Treating cancer cells with miR-145 will cause a shift to regulated growth characteristic of differentiation rather than the stem-like growth characteristic of both cancer cell growth and that of undifferentiated stem cells. Comparison of factors secreted by naive cancer cells and those treated with miR-145 would identify those agents responsible for promoting stem cell and cancer cell growth. They would be present in the untreated Ca CM and absent from the treated Ca CM. Identification could be accomplished by the same sort of protein separation then sequencing or mass spec analysis. Components could be separated on a gel, protein bands unique to the untreated Ca CM would be excised from the gel then analyzed by micro sequencing or mass spec.

In parallel, conditioned media from undifferentiated stem cells would be compared to conditioned media collected from stem cells treated with an agent that initiates differentiation, such as the MUC1* extra cellular domain peptide. In this case, the components uniquely or preferentially secreted by the untreated stem cells would be those desirable as agents to promote stem cell growth or induce pluripotency. Molecules that suppress these agents would be used as cancer therapeutics. In contrast, those components uniquely or preferentially secreted by the differentiating stem cells would be desirable as agents to treat cancer. Similarly, molecules that suppress these agents would be used to promote the growth of stem cells or to induce pluripotency.

Regulatory nucleic acids, such as micro RNAs, that either promote or suppress stem-like growth, i.e. stem or cancer cell growth, would be identified as described above with the exception that rather than analyzing secretions from the cells, the nucleic acids would be extracted and analyzed. For example, the technique known as Deep Sequencing and total transcriptome analyses can be performed to identify those regulatory RNAs that are either up- or down-regulated when stem-like growth is suppressed. Regulatory RNAs that are upregulated when stem cells differentiate such as miR-145 could be used as anti-cancer treatments. Similarly, molecules including siRNAs that suppress these micro RNAs can be used to promote or induce pluripotency. Regulatory nucleic acids that are upregulated in undifferentiated stem cell growth and cancer cell growth would be targeted for silencing or suppression in treatments of cancer or to synchronize initiation of differentiation of stem cells.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of culturing, expanding or growing embryonic stem cells, embryonic stem-like cells or induced pluripotent stem cells on a surface, comprising a. exposing the embryonic stem cells, embryonic stem-like cells, or induced pluripotent stem cells to a surface coated with a Muc1 or Muc1* ligand;

b. adding medium, and c. culturing the exposed cells, wherein the cells remain undifferentiated.

2. The method according to claim 1, wherein the surface is a membrane or a porous surface.

3. The method according to claim 1, wherein the surface is further coated with extracellular matrix or a component of extracellular matrix.

4. The method according to claim 3, wherein the component of extracellular matrix is RGD sequence containing peptides, poly-Lysine, collagen, laminin, Matrigel™ or Matrigel™-like substances.

5. The method according to claim 3, wherein the extracellular matrix is Matrigel™ or Matrigel™-like substance.

6. The method according to claim 1, wherein the ligand binds to the surface directly or indirectly through an intermediary.

7. The method according to claim 6, wherein the intermediary is a chemical linker or another protein or a combination thereof.

8. The method according to claim 7, wherein the protein is protein A or protein G.

9. The method according to claim 7, wherein the linker is photo or chemically sensitive.

10. The method according to claim 6, wherein the ligand or the intermediary is non-specifically adsorbed to the surface, or is covalently coupled or attached to the surface through an affinity tag-binding partner interaction.

11. The method according to claim 1, wherein the ligand is linked to a polymer.

12. The method according to claim 1, wherein the ligand is an antibody or a growth factor.

13. The method according to claim 12, wherein the antibody specifically binds to PSMGFR or C-10 PSMGFR.

14. The method according to claim 12, wherein the growth factor is wild-type NM23, or NM23-S120G mutant, or bFGF.

15. The method according to claim 1, wherein the surface is not Matrigel™.

16. The method according to claim 1, wherein the cell is cultured without fibroblast feeder cells.

17. The method according to claim 1, wherein the cell is removed from the surface without manual dissection.

18. A method of culturing, expanding or growing embryonic stem cells, embryonic stem-like cells or induced pluripotent stem cells on a surface, comprising a. exposing the embryonic stem cells, embryonic stem-like cells or induced pluripotent stem cells to a surface coated with an extracellular matrix a component of extracellular matrix;

b. adding medium containing a Muc1 or Muc1* ligand; and c. culturing the exposed cells, wherein the cells remain undifferentiated.

19. The method according to claim 18, wherein the agent is an antibody.

20. The method according to claim 18, wherein the agent is wild-type NM23 or NM23-S120G mutant.

21. The method according to claim 18, wherein the surface is not Matrigel™.

22. The method according to claim 18, wherein the cell is cultured without fibroblast feeder cells.

23. The method according to claim 18, wherein the cell is removed from the surface without manual dissection.

24. The method according to claim 18, wherein the surface is a membrane or a porous surface.

25. The method according to claim 18, wherein the component of extracellular matrix is RGD sequence containing peptides, poly-Lysine, collagen or laminin.

26. The method according to claim 18, wherein the extracellular matrix is Matrigel™ or Matrigel™-like substance.

27. A method of culturing, expanding or growing embryonic stem cells, embryonic stem-like cells or induced pluripotent stem cells on a surface, comprising culturing the embryonic stem cells, embryonic stem-like cells or induced pluripotent stem cells in MUC1*-positive cell conditioned media, wherein the cells remain undifferentiated.

28. The method according to claim 27, wherein the MUC1*-positive cells are cancer cells.

29. The method according to claim 28, wherein the MUC1*-positive cells are selected from T47D, ZR-75-30, or ZR-75-1.

30. The method according to claim 27, wherein the surface is a membrane or a porous surface.

31. The method according to claim 27, wherein the surface is coated with an extracellular matrix or a component of extracellular matrix.

32. The method according to claim 31, wherein the component of extracellular matrix is RGD sequence containing peptides, poly-Lysine, collagen or laminin.

33. The method according to claim 31, wherein the extracellular matrix is Matrigel™ or Matrigel™-like substance.

34. The method according to claim 27, wherein the surface is not Matrigel™.

35. The method according to claim 27, wherein the cell is cultured without fibroblast feeder cells.

36. The method according to claim 27, wherein the cell is removed from the surface without manual dissection.

* * * * *